United States Patent [19]
Bacus et al.

[11] Patent Number: 6,031,930
[45] Date of Patent: *Feb. 29, 2000

[54] METHOD AND APPARATUS FOR TESTING A PROGRESSION OF NEOPLASIA INCLUDING CANCER CHEMOPREVENTION TESTING

[75] Inventors: James W. Bacus, Oakbrook; James V. Bacus, Downers Grove, both of Ill.

[73] Assignee: Bacus Research Laboratories, Inc., Lombard, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/701,974

[22] Filed: Aug. 23, 1996

[51] Int. Cl.⁷ .......................... G06K 9/00; A61K 35/12; A01N 1/02

[52] U.S. Cl. .......................... 382/133; 382/284; 382/308; 424/573; 435/1.1

[58] Field of Search .......................... 250/461.2; 348/79, 348/588; 356/39; 364/922, 922.2; 382/128, 133, 134, 284, 132, 130, 131, 171, 172, 173, 189, 209, 218, 282, 286, 299, 308; 395/924; 435/509, 515–17, 129–131, 1.1; 345/115, 117; 424/572, 573

[56] References Cited

U.S. PATENT DOCUMENTS 3,999,047  12/1976  Green .................................. 235/151.3
4,150,360   4/1979  Kopp et al. ........................ 340/146.3 P (List continued on next page.)

OTHER PUBLICATIONS

"Biomarkers of Premalignant Breast Disease and Their Use as Surrogate Endpoints in Clinical Trials of Chemopreventive Agents" *The Breast Journal* vol. 1, No. 4, pp. 228–235 (1995), Charles W. Boone and Gary J. Kelloff, 8 pages.

"Development of Breast Cancer Chemopreventive Drugs", *Journal of Cellular Biochemistry*, 17G:2–13 (1993), Gary J. Kelloff, et al., 12 pages.

(List continued on next page.)

*Primary Examiner*—Jon Chang
*Assistant Examiner*—Jayanti K. Patel
*Attorney, Agent, or Firm*—Fitch, Even, Tarin & Flannery

[57] ABSTRACT

A system is provided for analysis of neoplasia in tissue at a very early stage as well as later stages of its progression and for reporting the progression or regression of the neoplasia. The system performs multi-parametric measurements of the morphological structure and texture of the tissue structure and correlates these measurements on a common morphological grading scale. The system performs certain tissue measurements which are more highly discriminating for one kind of neoplasia and performs other tissue measurement, which are more highly discriminating, for another kind of neoplasia. Diverse tissue measurements may be made on diverse tissue types such as breast, colon, or cervix tissue, etc. from animals or humans which tissue has subjected to different carcinogens or chemopreventive agents. The measurements are made in different units and on different scales; and then these measurements are combined and reported on a valid, objective, common, universal scale. Microscopic images of stained neoplastic tissue sections are optically and microscopically scanned to provide electronic tissue sample images that are electronically recorded. Then, morphometric features of tissue sample images are measured in first unit vales and texture measurements of the tissue samples, such as a Markovian texture measurement. Usually, normal tissue samples and abnormal cancerous tissue samples are analyzed using the same morphometric and texture measurements and their respective results are reported onto a grading common scale so that progression of the cancer can be ascertained relative to the normal tissue.

46 Claims, 17 Drawing Sheets

U.S. PATENT DOCUMENTS

| | | | |
|---|---|---|---|
| 4,199,748 | 4/1980 | Bacus | 340/146.3 CA |
| 4,213,036 | 7/1980 | Kopp et al. | 235/92 PC |
| 4,523,278 | 6/1985 | Reinhardt et al. | 364/413 |
| 4,742,558 | 5/1988 | Ishibashi et al. | 382/240 |
| 4,965,725 | 10/1990 | Rutenberg | 364/413.1 |
| 5,068,906 | 11/1991 | Kosaka | 382/48 |
| 5,072,382 | 12/1991 | Kamentsky | 364/413.08 |
| 5,073,857 | 12/1991 | Peters et al. | 364/413.1 |
| 5,099,521 | 3/1992 | Kosaka | 382/6 |
| 5,107,422 | 4/1992 | Kamentsky et al. | 364/413.08 |
| 5,163,095 | 11/1992 | Kosaka | 382/6 |
| 5,216,500 | 6/1993 | Krummey et al. | 358/93 |
| 5,218,645 | 6/1993 | Bacus | 382/133 |
| 5,257,182 | 10/1993 | Luck et al. | 382/224 |
| 5,260,871 | 11/1993 | Goldberg | 128/660.06 |
| 5,268,966 | 12/1993 | Kasdan | 382/6 |
| 5,287,272 | 2/1994 | Rutenberg et al. | 364/413.01 |
| 5,313,532 | 5/1994 | Harvey et al. | 382/15 |
| 5,333,207 | 7/1994 | Rutenberg | 382/6 |
| 5,473,706 | 12/1995 | Bacus | 382/133 |
| 5,505,946 | 4/1996 | Kennedy et al. | 424/195.1 |
| 5,687,251 | 11/1997 | Erler et al. | 382/133 |
| 5,784,162 | 7/1998 | Cabib et al. | 356/346 |
| 5,796,861 | 8/1998 | Vogt et al. | 382/128 |

OTHER PUBLICATIONS

"Development of Surrogate Endpoint Biomarkers for Clinical Trials of Cancer Chemopreventive Agents: Relationships to Fundamental Properties of Preinvasive (Intraepithelial) Neoplasia", *Journal of Cellular Biochemistry,* Supplement 19:10–22 (1994), Charles W. Boone and Gary J. Kelloff, 13 pages.

"Markovian Analysis of Cervical Cell Images" *The Journal of Histochemistry and Cytochemistry* vol. 24, No. 1, pp. 138–144 (1976), Norman J. Pressman, 7 pages.

"Surrogate Endpoint Biomarkers for Phase II Cancer Chemoprevention Trials", *Joural of Cellular Biochemistry,* Supplement 19:1–9 (1994), Gary J. Kelloff, et al., 9 pages.

| Fig. 2a | Fig. 2b |

RAT ESOPHAGUS EXPERIMENT #1

FIELD DNA AND TEXTURE MORPHOMETRY
(HUMAN CERVIX)

0 NORMAL
3 CIN I
4 CIN II
5 CIN III

**TISSUE SECTION EDITING
(HUMAN CERVIX)**

EDITING TO BASEL LAYER
AT ORIGINAL RESOLUTION

EDIT TOOL

RECONSTRUCTED SECTION
DISPLAYED AT 1/16
ORIGINAL RESOLUTION

METHOD AND APPARATUS FOR TESTING A PROGRESSION OF NEOPLASIA INCLUDING CANCER CHEMOPREVENTION TESTING

BACKGROUND OF THE INVENTION

This invention relates to a method and apparatus for analysis of neoplasia in tissue and for pre-invasive cancer and for analysis of the effect of chemopreventive agents with respect to neoplasia.

Currently, there are on-going chemoprevention programs that involve the routine testing of chemopreventive agents with the aims of using such agents to reduce the incidence of cancer by stopping the cancer progression or to regress the cancer. These programs desire to test a very large number of chemopreventive agents which occur naturally in foods or drinks or synthesized drugs for their efficacy. Currently, there are a number of centers that are testing chemopreventive agents and that use pathologists to visually examine tissue and quantify the efficacy of these agents administered to animals or humans. These visual assessments are quite broad and are subjective and usually result in assessments such as nuclear grade, carcinoma in situ, preneoplastic intraepithelial neoplasia, etc. It will be appreciated that the limited ability of the human eye to make visual assessments often requires the neoplasia to reach an advanced state in its evolution before it can be assessed. However, it is preferred to quantitatively evaluate the evolution of neoplasia in its early stage of evolution. The earlier the effective evaluation, the better chance of halting the progression of premalignant cells to the malignant state and the earlier that the effectiveness of possible chemopreventive agents can be determined.

A number of benefits are obtained by an earlier evaluation of the effectiveness of a chemopreventive agent. First, a very substantial cost benefit results from the ability to quantitatively evaluate premalignant tissue if done after an animal or person has been treated for ten to twenty weeks rather than to wait for the current thirty to forty weeks, which is often the case for visual evaluation by a pathologist. Further, if the apparatus and methodology used are more sensitive or precise than those used by the pathologist, fewer subjects need to be tested. This reduces the cost of analysis with respect to a particular chemopreventive agent or subject, and allows for more analyses to be done at any given testing facility in a given time frame. Of course, obvious health benefits accrue from earlier detection of a precancerous condition and the ability to monitor more quickly and more precisely the effectiveness of chemopreventive treatment for a given patient.

An article by Boone and Kelloff, entitled "Development of Surrogate Endpoint Biomarkers for Clinical Trials of Cancer Chemopreventive Agents: Relationships to Fundamental Properties of Preinvasive (Intraepithelial) Neoplasia", describes chemoprevention as the prevention of clinical cancer by the administration of drugs or dietary constituents prior to or during the early phases of precancerous neoplasia, i.e., while the neoplastic process is still confined to the intraepithelial compartment and has not yet become invasive. Boone and Kelloff describe tissue and cell changes and the need for the development of surrogate endpoint biomarkers (SEBs), and divide the evolution of neoplasia as a continuum divided for convenience into five phases. In Phase I, genomic instability is present in an otherwise normal-appearing epithelium. In Phase II, clonal expansion of a mutated cell occurs. The individual cells are normal in appearance but crowded and disorganized in pattern, with compression of the surrounding normal cells. This is the classic benign epithelioma (aberrant crypt foci of the colon are an example). In Phase III, the cells develop abnormal morphology (described in detail below). Phase IV is marked by invasion, the classic criterion by which pathologists make the diagnosis of cancer; and in Phase V, there is wide-spread dissemination. The ideal SEB should detect early changes during the intraepithelial neoplastic period and should monotonically increase in magnitude with neoplastic growth. The present invention is directed to providing a method and apparatus to assay cellular or tissue changes associated with the early neoplastic process, i.e., Stages I, II or III, prior to invasiveness and to be useful for many different tissue types, e.g. breast tissue, colon tissue, prostate tissue, esophageal tissue, skin tissue, cervix tissue, etc. for animals as well as for humans.

One problem with assaying such a variety of tissues is a determination of what measurements or features are most relevant or robust for each given neoplasia in that tissue. The measurements that provide the highest discrimination will vary from one neoplastic tissue to another type of neoplastic tissue. It will be appreciated that the various tissue types described above, such as breast tissue, colon tissue, prostate tissue, esophageal tissue, skin tissue, and cervix tissue have different morphologies, and they undergo different neoplasias usually resulting from a cellular mutation rate as may be enhanced by a carcinogen or resulting from a cellular proliferation rate enhanced by sex hormones, irritant chemicals or inducers from chronic infection. Currently, there are no good objective biomarkers for such diverse neoplasias that can be done using equipment. There is a need to develop highly discriminating tests or measurements. Additionally, the tests or measurements for neoplasia will be done on different types of animals and on humans and at different clinical sites. Further, the measurements are often made when the change in the neoplasia is quite small, such as when the neoplasia is incipient or because sequential tests are performed at close time intervals to ascertain if the progression of neoplasia has been slowed, stopped or regressed. The neoplasias may have distinct appearances as do their respective tissues. To be highly discriminating for such diverse tissues and diverse neoplasias, there is a need for a system which performs highly discriminating measurements for each particular neoplastic tissue. It has been found that some measurements are very discriminating for some tissues neoplasias but not very discriminating for other neoplasias.

Assuming that appropriate discriminating measuring techniques and data are found, there still is a problem of how to grade or report these diverse test results which are so disparate in form. That is, linear measurements, area measurements, density measurements, surface roughness or texture measurements are made in diverse units, scales and magnitudes; and there exists the problem of how to coherently combine these results into a common scale that will be meaningful, easily understood and easily interpreted by pathologists or clinicians. For example, it would be best if the common scale would be valid and useful for evaluating, for example, thirty (30) different agents for skin precancerous tissue, twenty (20) different agents for esophageal precancerous tissue, and fifty (50) precancerous agents for precancerous colon cancer. Thus, there is a need for a system where the results of the measurements are standardized and objective and are easily conveyed to clinicians and others and will provide them with an understanding of a chronology of the effects of small treatment doses of one or more chemopreventive agents on precancerous tissue.

SUMMARY OF THE INVENTION

In accordance with the present invention, a method and apparatus are provided for analysis of neoplasia in tissue at a very early stage as well as later stages of its progression and includes an easily understood reporting of the progression or regression of the neoplasia. The present invention provides a fast and cost-effective analysis of the efficacy of or lack of efficacy of chemopreventive agents with respect to neoplasia. This has been achieved by an objective analysis system that performs multi-parametric measurements of the morphological structure and texture of the tissue structure itself and correlates them to a simple morphological grading scale. Further, this analysis has been achieved by the determination of and the selective measurement of those features or attributes which are most discriminating for a given kind of neoplastic tissue to show the progression of neoplasia in the tissue. It has been determined that certain tissue texture measurements are more highly discriminating for certain neoplasias and that other tissue measurements are more discriminating for other neoplasias. The present invention has determined which measurements are most highly discriminating for certain neoplasias in certain tissues and allows a selection from a large menu of multi-parametric measurements for the respective different ones of the neoplastic tissues. Further, this invention provides a method of and apparatus for rapidly and automatically performing scanning and data acquisition for these assays in a cost-effective manner.

The present invention also relates to a method and apparatus for combining several diverse measurements results in different units and on different scales into a valid, objective and common universal scale which is useful not only in grading a particular neoplasia in tissue but is also useful for grading other neoplasias in tissues analyzed with other discriminating measurement. This common scale is relative to and self-adjusts to the respective normal morphology characteristics and differing heterogeneity of different tissue structures. In accordance with the present invention, a sound and universal morphological grading system has been devised to combine onto a common scale the various test results made of diverse tissue types, such as breast tissue, colon tissue, cervix tissue, etc. and on different types of animals and humans as well as with different carcinogens or chemopreventive agents. That is, the present invention allows one to analyze and measure the texture of a particular tissue having neoplasia, with a number of test results in different units and one different scales and combine them into a common score on a common scale. Also, the present invention provides a common scale and score for various neoplasias in different tissues and relates them to a common scale wherein their relationship to an invasive score can be easily understood. Stated differently, different test measurements on different neoplasias may be plotted on the same score or scale so that each neoplasia's progression or regression relative to a preinvasive state is easily understood. Such a common scale allows an objective comparison of one chemopreventive agent versus another chemopreventive agent, and between the efficacy of such agents on animal or human neoplastic tissue.

In the preferred apparatus and embodiment of the invention, a field of tissue is scanned by a microscope, and the scanned images are digitized, displayed and stored electronically. The stored tissue images are then optionally edited to isolate for analysis the basal layer and tissues evolving therefrom. The edited images are then measured for morphometric and texture features that are preselected as being highly discriminating for the kind of neoplastic tissue being analyzed. The measurements may be performed on entire microscope fields of imaged cell objects or on individual cell objects of the fields.

In accordance with another aspect of the invention, the preferred analysis is achieved by performing texture and morphometry measurements on normal tissue of the kind under consideration and then performing the same morphometry and texture measurements on a second tissue which is usually known to be a neoplastic tissue or suspected to be a neoplastic tissue. Then, the mean and standard deviation for each normal tissue measurement are determined. The mean for the second tissue is subtracted and divided by the standard deviation of the normal tissue to provide an individual Z-scale morphometric score. Individual Z-scale scores are averaged to provide a final score for the second tissue that is hereinafter is called a "Morphometric Z-scale Score". By way of example only, the morphometric Z-scale score for invasive neoplasia would be about a 7 or a 8 relative to zero or about zero score for a normal tissue so that there is sufficient breath of scale to distinguish on the scale incipient neoplasias close to zero and to distinguish small incremental changes in neoplasia as may occur subsequently to an application of an effective chemopreventive agent for a short period of time. On the other hand, the application of a highly carcinogenic or neoplastic enhancing agent may provide a widely differentiating morphometric Z-scale score over a short period of time.

In the present invention, each of the various suspected neoplastic tissues from the skin, cervix, colon, breast, etc. may be examined using different morphometric and texture features which are more powerful or discriminating for that kind of tissue. Even though different features are measured for these diverse neoplastic tissues, the above-described normalizing allows the results of each assay to be scored on the same morphometric Z-scale, and automatically compensates for normal heterogeneity of different tissues.

Referring now in greater detail to the illustrated embodiment of the invention, neoplastic tissue sections are cut on edge and stained; and a step of editing is done interactively by a person who views visually and edits 100 to 400 digitized tissue images. The magnification used by the microscope allows the detection of features that are not seen by the human eye without magnification; and the analysis is done using these magnified features. Because 100 to 400 high resolution images of a neoplastic tissue is too large for an ordinary monitor, it is preferred to decrease the magnification of the displayed image so that a large segment of suspected neoplastic tissue comprising many images can be seen at once by the operator. The operator may then edit the tissue image on the monitor to exclude muscle, debris and other cell images leaving the basal layer image and those tissue cell images evolving from the basal layer for the morphometric and texture analysis at the higher resolution.

It has been found that the measurements and tests used and needed are those that discriminate more texture and more granules which appear in neoplastic tissue than appear in normal tissue. That is, the malignant cells have more dark granules and a more "clump-like" or clumpy appearance and also a more "coarse" appearance. By way of analogy, the coarseness may be thought of as a serrated edge of a saw blade that has teeth defined by a number of uniform size peaks and valleys with occasional larger teeth projecting above the uniformly-sized teeth. The measure of the number of such oversized peaks, the distance therebetween, the length of teeth slope, the depth of the valleys, and the height of the peaks provide data as to the abnormal morphology of the neoplasia. The present invention may use some conventional tests and measurements, such as area measurements and summed optical densities, but a number of other specialized tests have been developed to quantify texture. Some known "Markovian Texture" measurements may also be used. For the most part, the selection of which particular measurements will result in highly discriminating Z-scores is one of trial and error.

The preferred texture measurements are usually taken in orientation to the basal layer and will have adjustable thresholds set for a particular tissue. Typically, the test measurements used are selected from a menu of as many as one hundred (100) test measurements; but usually include ten (10) or less test measurements which are defined hereinafter) selected from a group comprising area; summed optical densities; run length; configurable run length; valley, slope or peak; and Markovian Textures.

BRIEF DESCRIPTION OF THE DRAWINGS

FIG. 1A is a perspective view, having portions broken away, of an automatic optical input subsystem of the apparatus for assaying biological specimens shown in FIG. 1;

DETAILED DESCRIPTION OF THE PREFERRED EMBODIMENT

Figure 1:
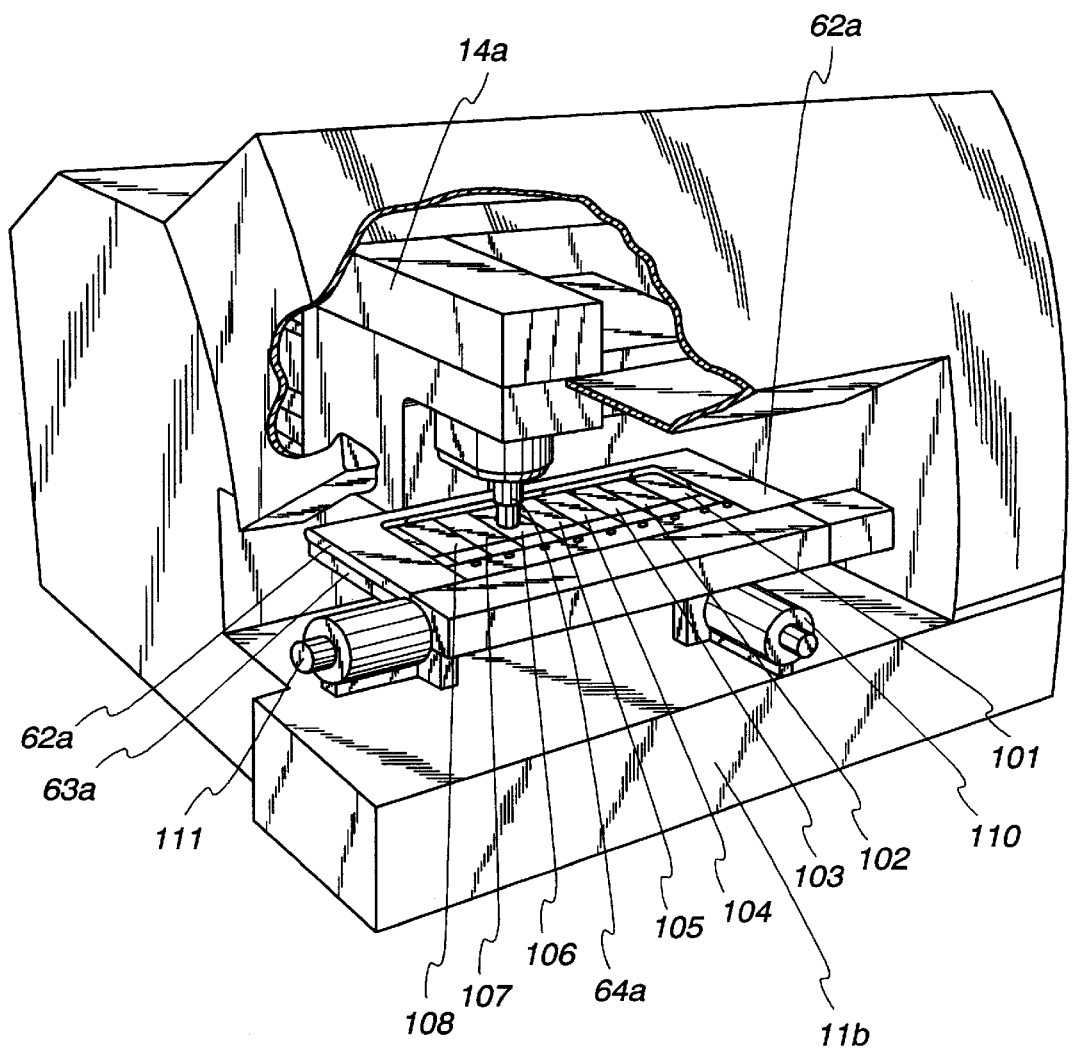
FIG. 1 is a perspective view of an apparatus for assaying biological specimens embodying the present invention.

The present embodiment assays tissue samples to identify a progression of neoplasia therein and is used with laboratory animals, such as rats, to test possible chemopreventive agents for efficacy. The embodiment is also used to identify early neoplasia in other populations, including humans, to provide early disease detection which can prompt early treatment.

The neoplasia identification of the embodiment begins with a tissue sample which is stained or otherwise prepared for microscopic examination. The tissue samples are prepared so that a basal layer and cells evolving therefrom are presented to the microscope objective. The microscopic examination is performed by automated apparatus such as that described in U.S. Pat. No. 5,473,706 issued Dec. 5, 1995.

The automated apparatus acquires optical density data from the stained tissue sample in a plurality of image frames, each about 90 ×150 microns. The image frames of most interest are acquired along the basal layer of the tissue sample. Accordingly, when the basal layer is relatively linear, the image frames are acquired in abutting fashion along the basal layer. When the basal layer is more irregular, abutting image frames are acquired in successive raster-like rows to cover the area of the sample. The acquired data is digitized and stored for editing and analysis. In an editing process, image frames which do not contain information helpful to the analyses are excluded in their entirety. Further, cell objects in selected image frames are erased and the remainder of the image frame is stored for later use.

After image frame acquisition and editing the analysis of the data they contain begins. A plurality of morphometric and texture analyses, such as cell object area, optical density, optical density per unit area, run length, configurable run length, valley-slope-peak and Markovian, may be performed on the image frames. The particular analyses to be performed for each type of tissue are selected for that type of tissue to be indicative of neoplasia. As described in greater detail below, the selection of analyses may result in a different set of analyses being performed for different tissue samples.

The analyses are performed on a per-image frame resulting in a mesaured quantity being stored for each analyzed image frame for each analysis performed. The analysis on a per-image frame basis has been found to provide results which identify neoplastic growth more readily than measuring only selected cell objects.

Image Acquisition Apparatus

With the multitude of different tests being performed with many having different units of measurement, analyzing the results is difficult. The present embodiment includes a data normalizing method for use in producing a morphological Z-score which uses a single number to represent the analysis of a tissue sample. Examples are provided herein which show the efficacy of the present embodiment to detect neoplasia.

The preferred embodiment disclosed herein is used for the assay of tissue sections for neoplasia. The tissue samples to be analyzed in the preferred embodiment are stained using the Feulgen technique for DNA which is described in detail in U.S. Pat. No. 4,998,284, issued Mar. 5, 1991 to Bacus which is hereby incorporated by reference. Other types of staining such as Hematoxylin and Eosin or Papanicolaou may be used within the scope of the present invention, as can any stain that enhances histological structure for images. The apparatus shown and described with regard to FIGS. 1–4 is used in the preferred embodiment to acquire image frames of tissue sample data. This apparatus includes a two-color optical system to enhance the optical characteristics of stained tissue samples; although, analysis by a single color is used primarily herein to determine optical densities.

Figure 2A:
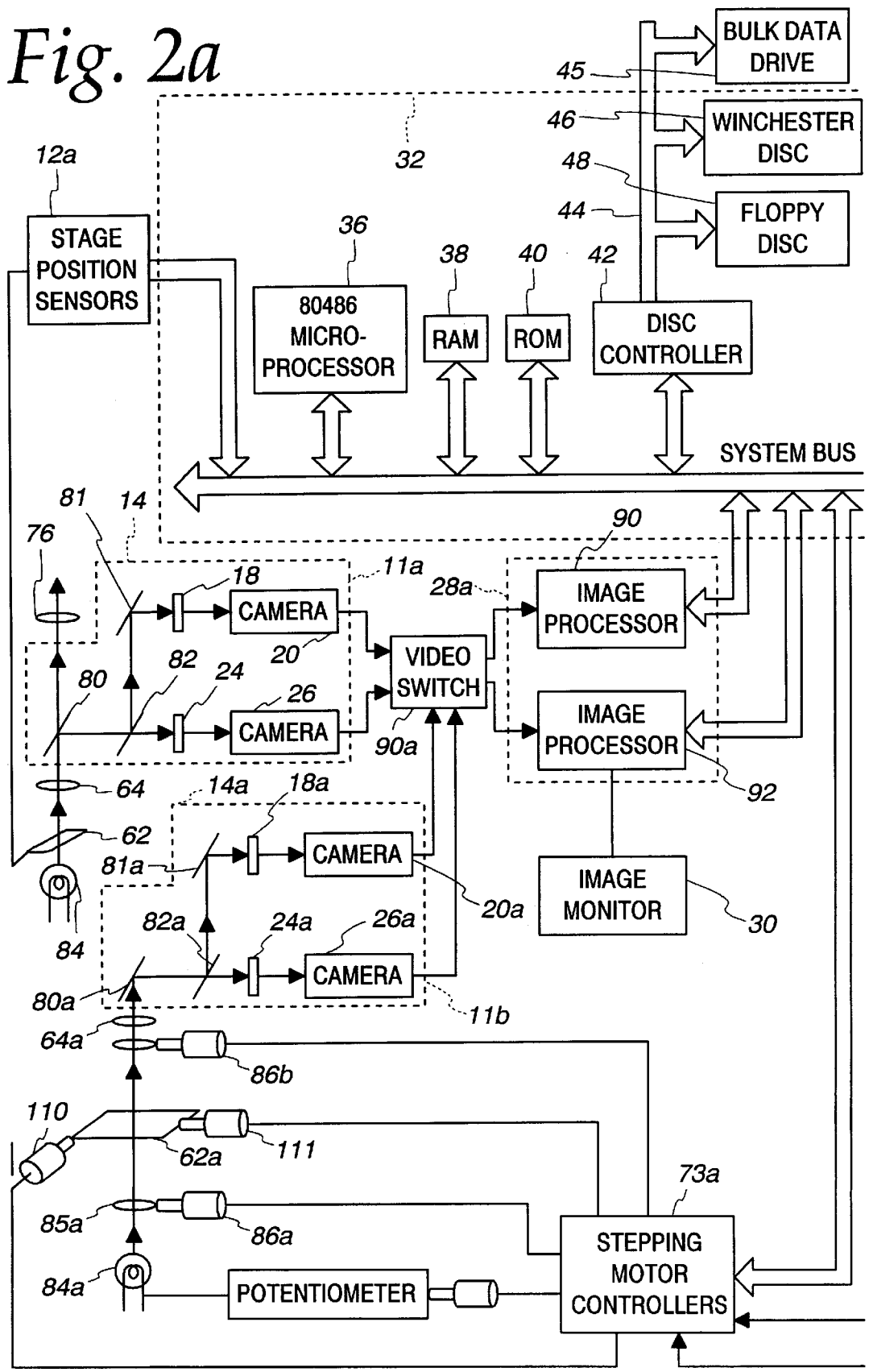
FIG. 2 is a block diagram of the apparatus shown in FIG. 1.
Figures 2, 2B:
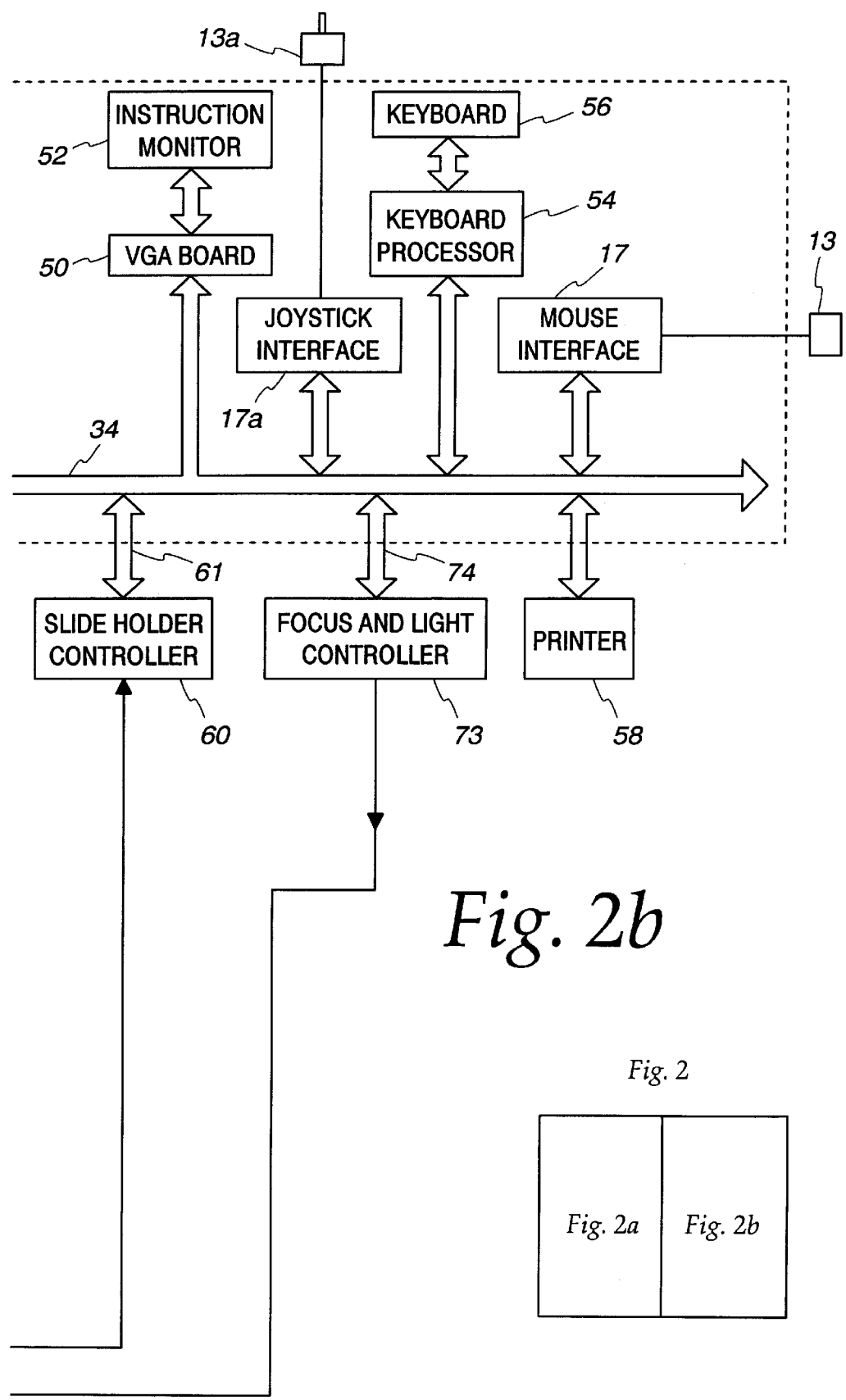
Figure 3:
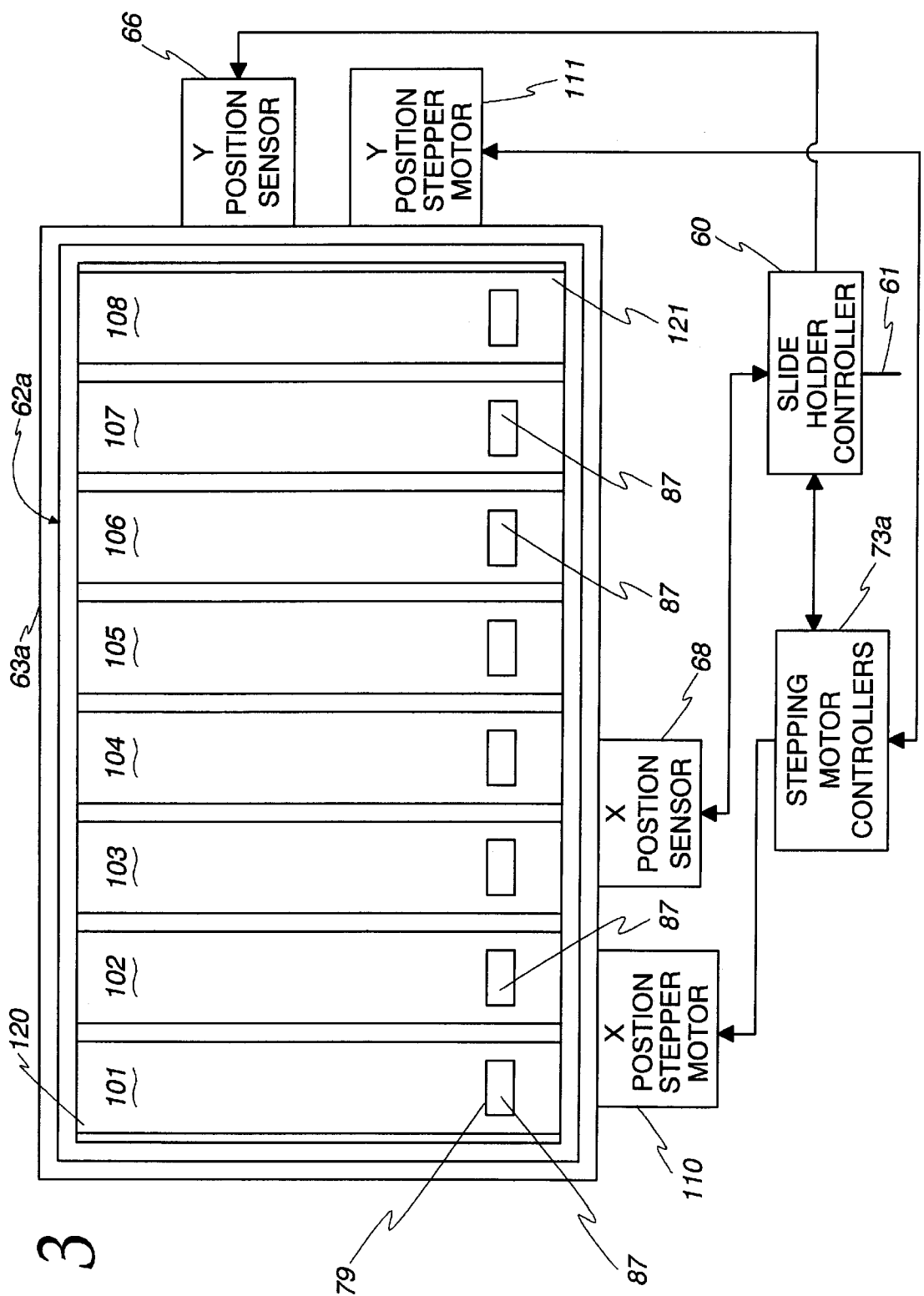
FIG. 3 shows a slide holder and associated control equipment of the apparatus shown in FIG. 1.

An apparatus for assaying biological specimens, and embodying the present invention and generally identified by numeral 10 is shown in perspective view in FIG. 1 and in block diagram form in FIG. 2. An interactive optical system 11a comprises an optical microscope 12, which may be of any conventional type, but in this embodiment, is a Riechart Diastar. An optical conversion module 14 is mounted on the microscope 12 to enhance the optically magnified image of cell samples viewed with the microscope 12. The optical conversion module 14, as may best be seen in FIG. 2, includes a beam-splitting prism 80 which conveys approximately 90% of the light into optical conversion module 14 and passes the remaining 10% to a microscope eyepiece 76. The light transmitted into module 14 is fed to a dichroic beam-splitter 82 which reflects a portion of the light to a television camera 20 via a red filter 18 and a mirror 81. The remaining portion of the light is filtered by a dichroic beam-splitter 82 and fed to a television camera 26 through a green filter 24. The dichroic beam-splitter 82 selectively passes light having wavelengths greater than approximately 560 nanometers to the filter 18 and having a wavelength of less than 560 nanometers to the filter 24. Thus, the dichroic beam-splitter 82 acts as a first color filter before the light reaches the color filters 18 and 24. Red filter 18 is a 620±20 nanometer bandpass optical transmission filter which provides a high contrast image to the camera 20. As shown in FIG. 2, the camera 20 generates an NTSC image signal which is fed through an optical signal switch 90a to an image processor 90 of an image processor module 28 (FIG. 2). Green filter 24 is a 500±20 nanometer narrow bandpass optical transmission filter which provides a high contrast image to a camera 26. The camera 26 then feeds an NTSC image signal through the optical signal switch 90a to an image processor 92. Both of the image processors 90 and 92 contain analog to digital converters for converting the analog NTSC signals to a digitized 384 by 485 array pixel image. The center 256 by 256 array of pixels from this digitized image is then stored within frame buffers internal to the image processors 90 and 92. The visual image represented by the 256 by 256 array of pixels is referred to as an image field. In the present embodiment a pixel has a height of approximately 0.34 micron and width of approximately 0.5725 micron, so that an image field represents approximately an 87.04 by 146.54 micron portion of the tissue section.

Each of the image processors 90 and 92 is a Model AT428 from the Data Cube Corporation, and includes six internal frame buffers. The image processors 90 and 92 are connected to a system bus 34 of a computer 32. The frame buffers of image processors 90 and 92 are mapped into the address space of a microprocessor 36 in computer 32 to provide easy access for image processing. Additionally, an image monitor 30 is connected to image processor 92 and displays a cell sample image field stored in a predetermined one of the frame buffers. The storage of an image field representation into the predetermined frame buffer is described later herein.

The automatic optical conversion module 11b, as may best be seen in FIG. 2, includes a prism 80a which conveys the light into optical conversion module 14a. The light transmitted into module 14a is fed to a dichroic beam-splitter 82a which reflects a portion of the light to a television camera 20a via a red filter 18a and a mirror 81a. The remaining portion of the light is filtered by a dichroic beam-splitter 82a and fed to a television camera 26a through a green filter 24a. The dichroic beam-splitter 82a selectively passes light having wavelengths greater than approximately 560 nanometers to the filter 18a and having a wavelength of less than 560 nanometers to the filter 24a. Thus, the dichroic beam-splitter 82a acts as a first color filter before the light reaches the color filters 18a and 24a. Red filter 18a is a 620±20 nanometer bandpass optical transmission filter which provides a high contrast image to the camera 20a. As shown in FIG. 2, the camera 20a then generates an NTSC image signal which is fed through the optical signal switch 90 to the image processor 90 of the image processor module 28 (FIG. 2). Green filter 24a is a 500±20 nanometer narrow bandpass optical transmission filter which provides a high contrast image to a camera 26a. The camera 26a then feeds an NTSC image signal through the optical signal switch 90a to the image processor 92.

The above-described apparatus accumulates image information at cameras 20 and 20a from red filters 18 and 18a and at cameras 26 and 26a from green filters 24 and 24a. The analysis performed herein uses primarily the image produced by the red filters 18 and 18a and converted by cameras 20 and 20a. As a result, a data acquisition having only the filters 18 and 18a with associated cameras 20 and 20a is sufficient for performing analyses herein described.

The microprocessor 36 of computer 32 is an Intel 80486 microprocessor which is connected to the system bus 34. The optical switch 90a, under control of the microprocessor 36, selects the signal from interactive unit 11a or automatic unit 11b to be fed to the image processors 90 and 92. A random access memory 38 and a read only memory 40 are also connected to the system bus 34 for storage of program and data. A disk controller 42 is connected by a local bus 44 to a Winchester disk drive 46 and to a floppy disk drive 48 for secondary information storage. Advantageously, local bus 44 is connected to a moveable media bulk data drive 45 such as an optical write once read many times (WORM) drive for image field recording and retrieval.

A video conversion board 50, in this embodiment a VGA board, is connected to the system bus 34 to control an instruction monitor 52 connected to the VGA board 50. Operational information such as selection menus and reports of analysis are displayed on instruction monitor 52. A keyboard processor 54 is connected to the system bus 34 to interpret signals from a keyboard 56 connected to the keyboard processor 54. Input signals to microprocessor 36 are also generated by a hand control drive (mouse) 13 having a control button 15. Signals from mouse 13 and its button 15 are conveyed to bus 34 via a mouse interface 17. A printer 58 is connected to the system bus 34 for communication with microprocessor 36. The apparatus 10 also includes a joystick control device 13a of a type well known in the art. Signals from the joystick 13a are conveyed to bus 34 via a joystick interface 17a.

The automated image input subsystem 11b of apparatus 10 performs automated X-Y slide positioning, image focusing, light intensity adjustment and light color balancing functions. The X-Y slide position controlling apparatus is shown in FIGS. 1, 1A, 3 and 4, and includes a slide holder 62a capable of holding eight microscope slides 101 through 108 in side-by-side relationship such that the upper surfaces of the slides are substantially coplanar. Slide holder 62a, which is sometimes referred to as a flat bed carrier, is movably attached to the stage 65a of microscope objective 64a by means of a slide holder base 63a. The portion of slide holder 62a positionable with respect to microscope objective 64a is controlled by an X position stepper motor 110 and a Y position stepper motor 111 which are mechanically attached to base 63a. The stepper motors 110 and 111 are of the type known in the art which respond to pulse signals from a slide holder position controller 60. The actual X and Y positions of the slide holder 62a are sensed by an X position sensor 68 and a Y position sensor 66, respectively, which substantially continuously report position information to slide holder controller 60. In the present embodiment the slide holder 62a, base 63a, and position sensors 66 and 68 including limit switches and numbered 110 and 111 comprise a commercially available unit from Marzhauser Wetzlar GmbH Model EK8B-S4 with Model MCL-3 control units.

Responsive to appropriate stepper motor control signals, the slide holder base 63a is capable of placing substantially all of each of slides 101 through 108 under the objective 64a. Slide holder position controller 60 is connected to system bus 34 by means of a communication path 61. Microprocessor 36, as discussed later herein, transmits commands to slide holder position controller 60 specifying an X and Y position to place under the microscope objective 64a. Slide holder position controller 60 responds to such commands by transmitting to the X and Y stepper motors 110 and 111 the appropriate sets of pulse signals to move the slide holder 62a to the desired X-Y position. The actual position of slide holder 62a is checked by slide holder position controller 60 during and at the completion of movement. The slide holder position controller 60 also maintains an internal record of the X and Y position of the slide holder 62a which internal record can be read by microprocessor 36 via bus 34 and communication path 61.

Figure 4:
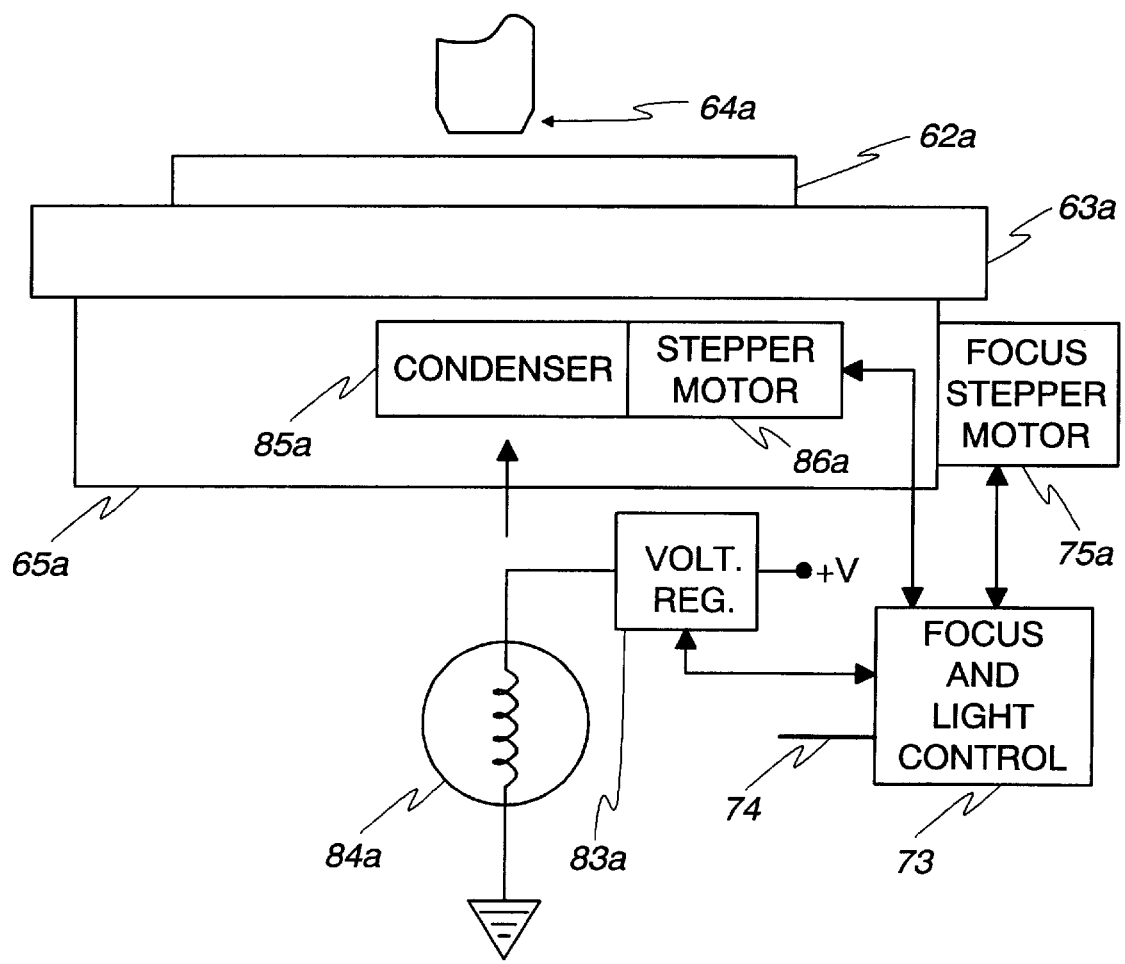
FIG. 4 is a block diagram view of focus and light control portions of the apparatus shown in FIG. 1.

The apparatus 10 also includes a focus and light controller 73 which controls the light intensity and color balance from the light source 84a, as well as the focus of the image field presented to microscope 12. Microprocessor 36 communicates with focus and light controller 73, via the system bus 34 and a communication path 74, to control the focus and light properties. FIG. 4 is a functional block diagram of focus and light controller 73 and its connection to objective 64a and to bus 34. The objective 64a includes a focus stepper motor 75a, which is controlled by focus and light controller 73 through the stepper motor controller 73a to raise and lower the stage 62a, and thereby raise and lower the microscope slides 101 through 108 carried by slide holder 62a. Microprocessor 36 includes a focus routine which is periodically performed during tissue analysis. When the focus routine is entered, microprocessor 36 reviews a digital representation of an image field from the image processors 90 and 92, and issues a command to focus and light controller 73, to raise or lower the stage by a specified amount. Focus and light controller 73 responsively transmits to focus stepper motor 75a electrical signals to implement the requested stage movement. By continued checking of the quality of the image field and adjustment of the up and down position of the slide holder 62a, microprocessor 36 brings the upper surface of the slide under the objective 64a into focus.

Microprocessor 36 also stores a target value for the light intensity which is to be maintained during tissue sample analysis. This stored light intensity value is used by microprocessor 36 in conjunction with an intensity function to regulate the intensity of light from light source 84a. When the intensity function of microprocessor 36 is enabled, the light intensity as represented by image fields from image processors 90 and 92 is determine. Any departure from the stored target light intensity value is corrected by sending intensity control commands to focus and light controller 73 which responds thereto by controlling a voltage regulator to increase or decrease the voltage applied to light source 84a. Voltage regulator 83 may be, for example, a standard rotatable voltage regulator which is rotated by a stepper motor operating under the control of electrical signals from focus and light controller 73.

Acquisition of Image Frames

Figure 5:
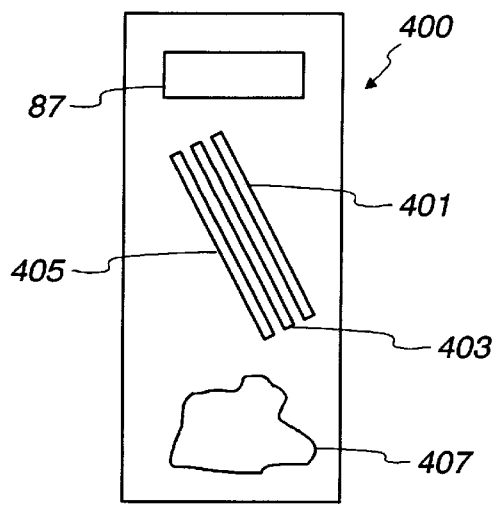
FIG. 5 is a plan view of a microscope slide with a tissue section placed thereon for use with the apparatus of FIG. 1.
Figure 6:
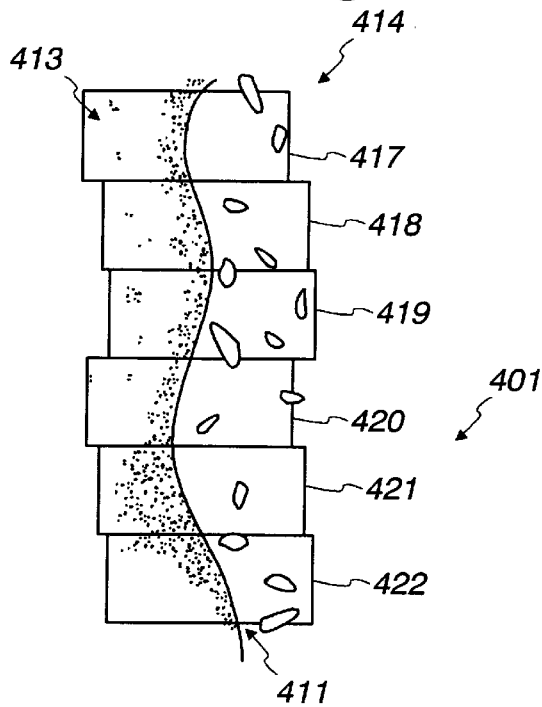
FIG. 6 shows a plurality of abutting image fields acquired for analysis.

FIG. 5 shows a microscope slide 400 prepared for the evaluation of rat esophageal tissue for neoplasia. Tissue sections 401, 403, and 405 of the entire rat esophagus are taken and placed on the slide 400. Also placed on the slide 400 is a control tissue sample 407 of, for example, rat liver cells about which the properties are well known and which can be used to calibrate the apparatus and the tests performed as is known. The tissue sections 401, 403 and 405 are taken and placed on the slide in such a manner that the basal layer of cells is substantially continuously observable. FIG. 6 shows a magnified portion of an esophageal tissue section such as section 401. The tissue section 401 is an epithelial section having a basement membrane 411 whith the basal layer of cells on one side 413 and supportive tissue cells on the other side 414. The basal layer of cells forms the inner layer of the esophagus and it is in this layer in which cells evolve to maintain the outer surface of the esophagus. After the tissue samples 401, 403, 405 and 407 are placed on slide 400 (FIG. 5), they are prepared with normal DNA Feulgen staining techniques in a manner in which all cell samples including the control cells 407 are stained by the same process. After staining, the tissue section is covered with a cover glass and made ready for testing.

The slide 400 is mounted in one of the slide positions, e.g. 102, of slide holder 62a which is, in turn, attached to base 63a so that slide 400 can be positioned under the objective 64a. The joystick 13a is used to control the position of slide 400 by controlling control unit 32 to energize motors 100 and 111 as previously discussed. The magnification of the microscope is set to 40X, corresponding to approximately the previously discussed 0.34 by 0.5725 micron pixel size, resulting in an image frame (256×256 pixels) of about 87.04 microns by 146.54 microns. In the manner previously described, the instrument is focused and light intensity is adjusted automatically to predetermined standards. The position of slide 400 is then adjusted to bring one of the esophageal tissue samples, e.g. 401, under the objective 64a and focus is again performed by the apparatus.

The primary interest in the present analysis is the basal layer on side 413 of the basement membrane 411 and the cells evolving from the basal layer. In tissue samples such as the rat esophagus of FIG. 6, the basal layer is somewhat continuous and linear and a plurality of abutting optical frames, e.g. 417–422, are imaged and a digital representation of the optical density of each image frame is generated and stored. In an analysis, between 100 and 400 such frame images along the basal layer are imaged and digitized. The digitized images represent the intensity of the light at each pixel on a linear scale represented by 8 bits. Thus, the stored image records the optical density of each of the 256×256 pixels in the image frame. After an image is digitized, it is stored in an addressable location in the system memory for later recall. The set of stored digital images make up the data used for later analysis. Also stored is a physical address of each optical frame on the tissue sample so that the whole image can later be reconstructed from the set of stored frame images. The individual digital values representing each pixel within each frame are also stored at individually addressable locations.

The selection of frames for imaging and storage may be done manually by an operator or automatically by the apparatus. In a completely manual operations, the human operator selects, by controlling the joystick 13a, each of the fields and marks them for digitizing. In a completely automatic system, the apparatus will image adjacent fields in an area identified as containing the basal layer or the apparatus could automatically follow the line of increased density (darkness) which represents the basal layer, producing a series of images as shown in FIG. 6. In a preferred image acquisition method, an operator first identifies generally the position of the basal layer by tracing it using the joystick. The apparatus records the X and Y coordinates of the traced line and after tracing, returns to digitize and store abutting frames along the recorded line.

Figure 7:
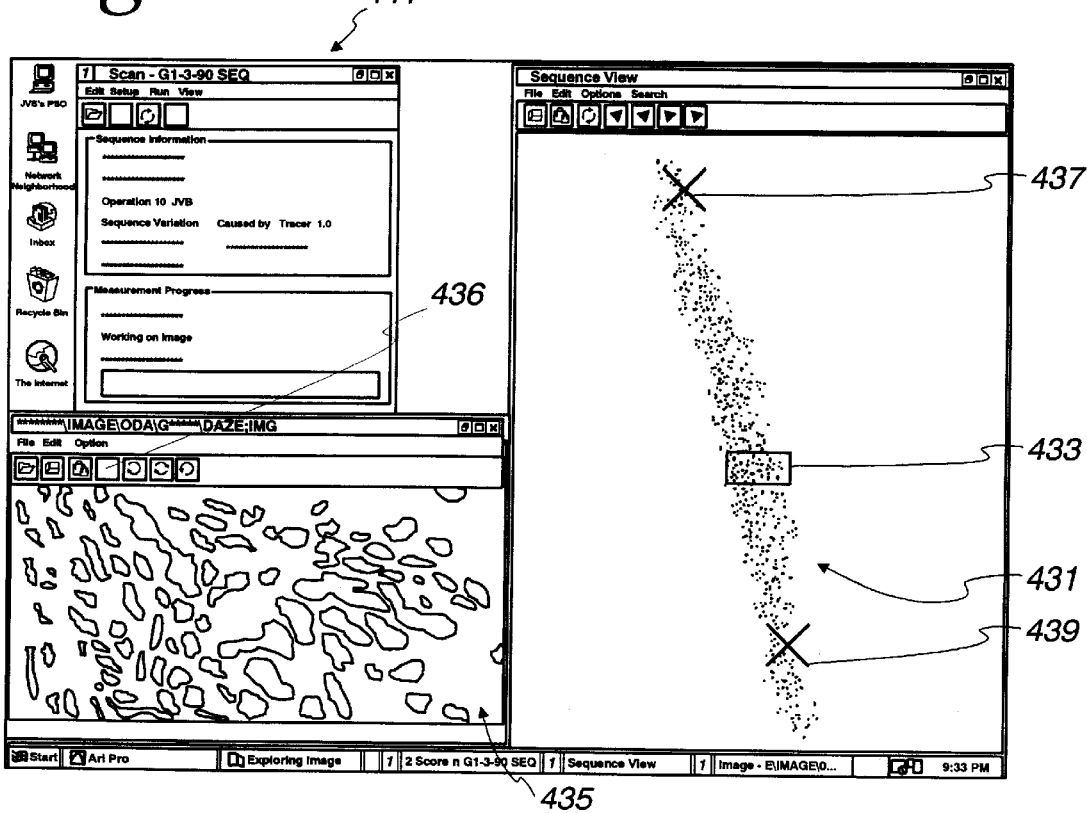
FIG. 7 shows a monitor screen on which is presented a mosaic of field images at reduced magnification and one field image in the present acquisition magnification.
Figure 8A:
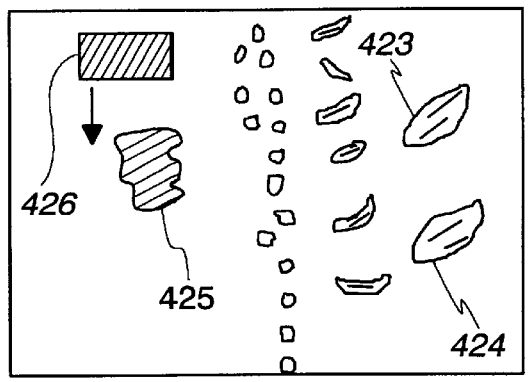
FIGS. 8A and 8B illustrate an edit mode of operation for working with displayed image frames.
Figure 8B:
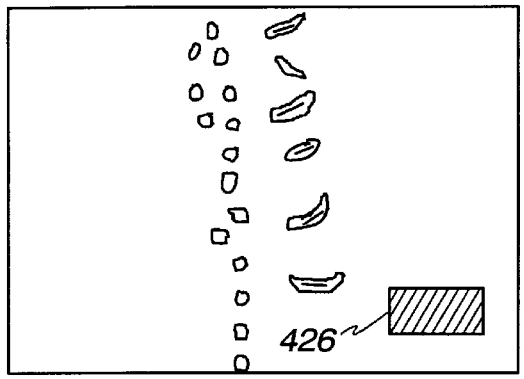
Figure 20A:
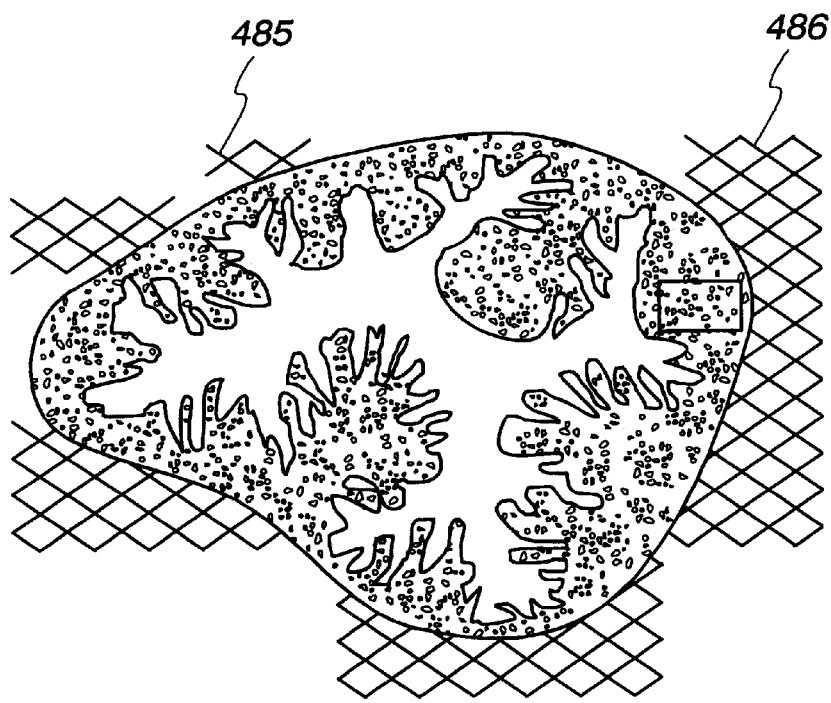
FIGS. 20A–D illustrate the raster method of image frame capture, editing and presentation.
Figure 20A:

The image acquisition phase of the procedure may continue with an optional editing phase. In other cases, the editing phase is omitted and the analysis process continues on all of the acquired images. At the beginning of the editing phase, a mosaic of tiles representing the images from the data acquisition is presented to an operator on the video display 30. The mosaic is presented with accurate image frame alignment so that the image, although reduced in magnification, appears substantially the same as the original tissue samples. FIG. 7 shows a mosaic 431 of frame images of rat esophagus tissue as displayed on monitor 30. A particular frame, as indicated by rectangle 433 of the mosaic 431, has been selected for a magnified view. The magnified view of frame 433 is presented in a field 435 of the display screen 30. When a magnified field 435 is presented, the operator can click on an eraser icon 436 and enter an edit mode in which the displayed individual image frame can be modified. The selected frame can be deleted entirely from the analysis, in which case it is marked with an X on the mosaic as shown at 437 and 439 in FIG. 7. The deleted frame may, for example, be one in which the tissue sample is broken or distorted or which contains some other flaw to cause it to have limited analysis value. In the edit mode the operator can also delete selected cell objects from the stored digital image. When the edit mode is optionally entered, an erasing cursor 426 is presented on the magnified image as shown in FIG. 8A, which erasing cursor can be moved by the computer mouse 13. As the erasing cursor 426 is moved on the image, the digital value of any pixel displayed at a position crossed by the erasing cursor 426, is set to "0" and remains "0" after the cursor moves on. Any object can be removed from the image field by the use of the erasing cursor. FIG. 8B shows the image field of FIG. 8A after the erasing cursor has been moved across the pixels of cell objects 423, 424 and 425 to remove them. The edited image 8B replaces the image 8A in the mosaic 431 and for later analysis.

the preceding example of mouse esophageal tissue (FIGS. 6–8) demonstrated the capture and editing of image frames by an operator identifying the relatively linear basal layer and the apparatus producing a series of abutting images along the identified layer. The present apparatus can also be used to capture and edit images in cases where a relatively linear basal layer is not present. The preferred embodiment can, at the operator's request, scan and image tissue samples in a raster manner as shown in FIG. 20A mouse colon cross sections. In the raster type scan the operator identifies the outer perimeter of the object to be scanned. The apparatus records the X and Y coordinate of the perimeter and then begins the image capture and digitizing at the upper left and proceeds across the object, within the identified perimeter with abutting image fields. When the right-most perimeter is reached the apparatus drops down one row of images and proceeds to capture and digitize abutting image fields from right to left and so on until the area within the identified perimeter is filled with abutting image fields.

Figure 20B:
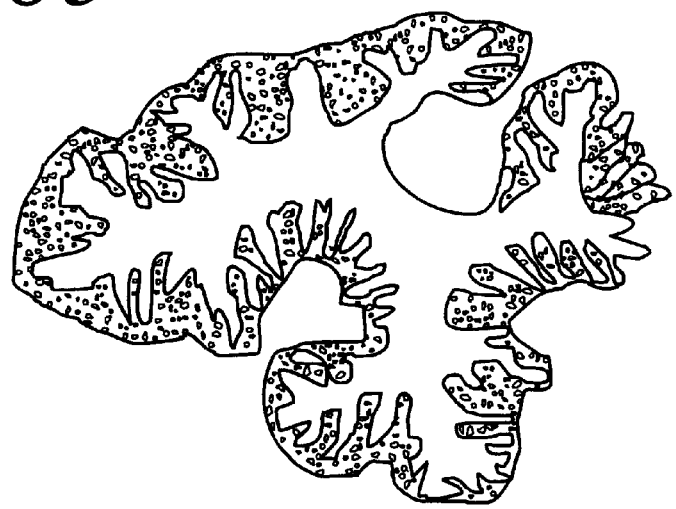
Figure 20D:
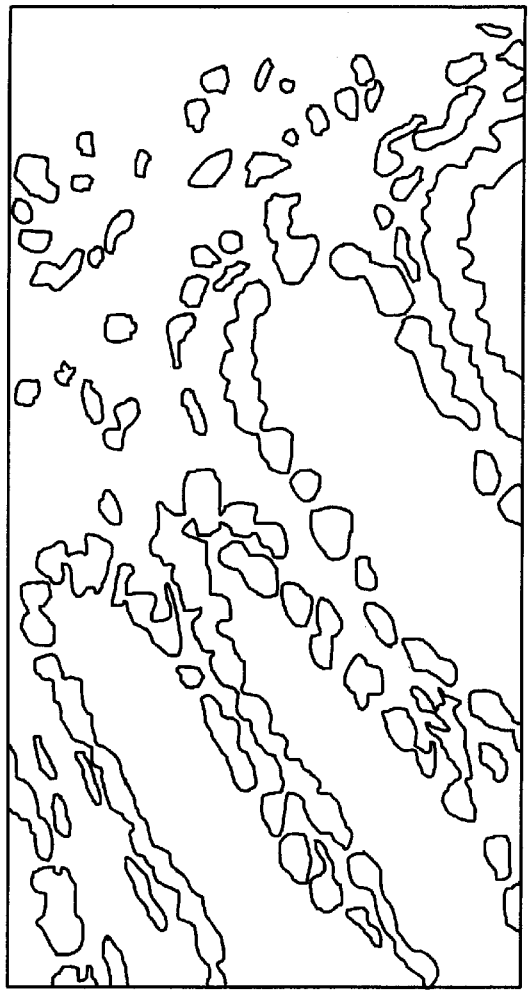
Figure 20C:
Figure 21:
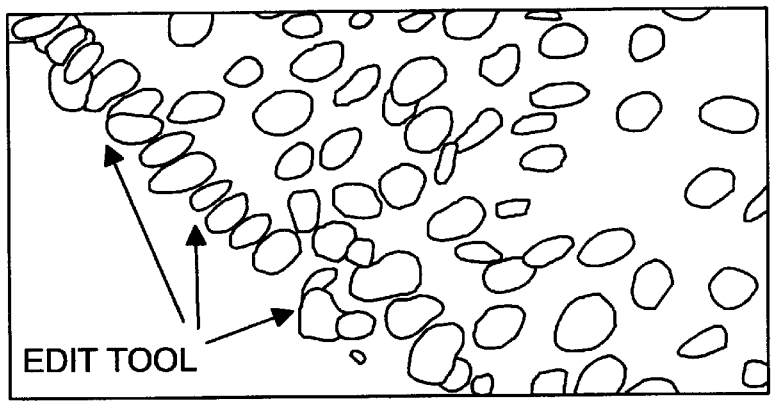
FIG. 21 shows the raster method applied to human cervix tissue.
Figure 21:
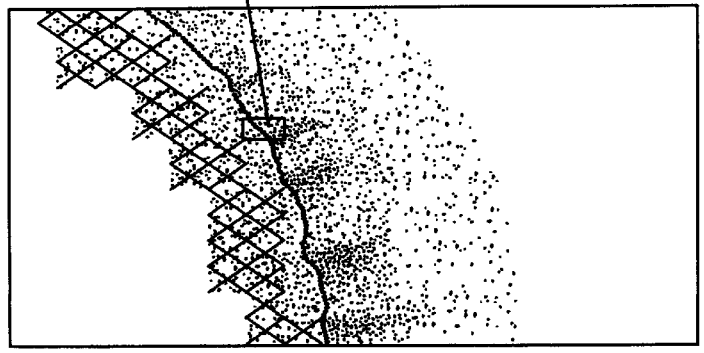

After the area of image fields has been captured and digitized, the editing process begins on a per-image frame basis. As shown with X's in FIG. 20A, some image frames, e.g. 485, 486, are completely removed from analysis by deleting them. After all unwanted image frames have been deleted, the remaining image frames can be individually selected and edited as described with regard to FIGS. 8A and B to remove unwanted cell objects. The selection of an image field 488 for display at an increased magnification (FIG. 20D) and editing with the erasing cursor 426 is shown in FIG. 20C. After all unwanted image frames have been deleted and unwanted cell objects removed from the remaining image frames, the individual image frames are presented on the display as an edited sample mosaic as shown in FIG. 20B. After editing, analysis proceeds image frame by image frame. The raster scan technique for image capture and analysis is also useful for human cervix tissue samples as represented at FIG. 21.

Image Frame Analysis

Figure 9:
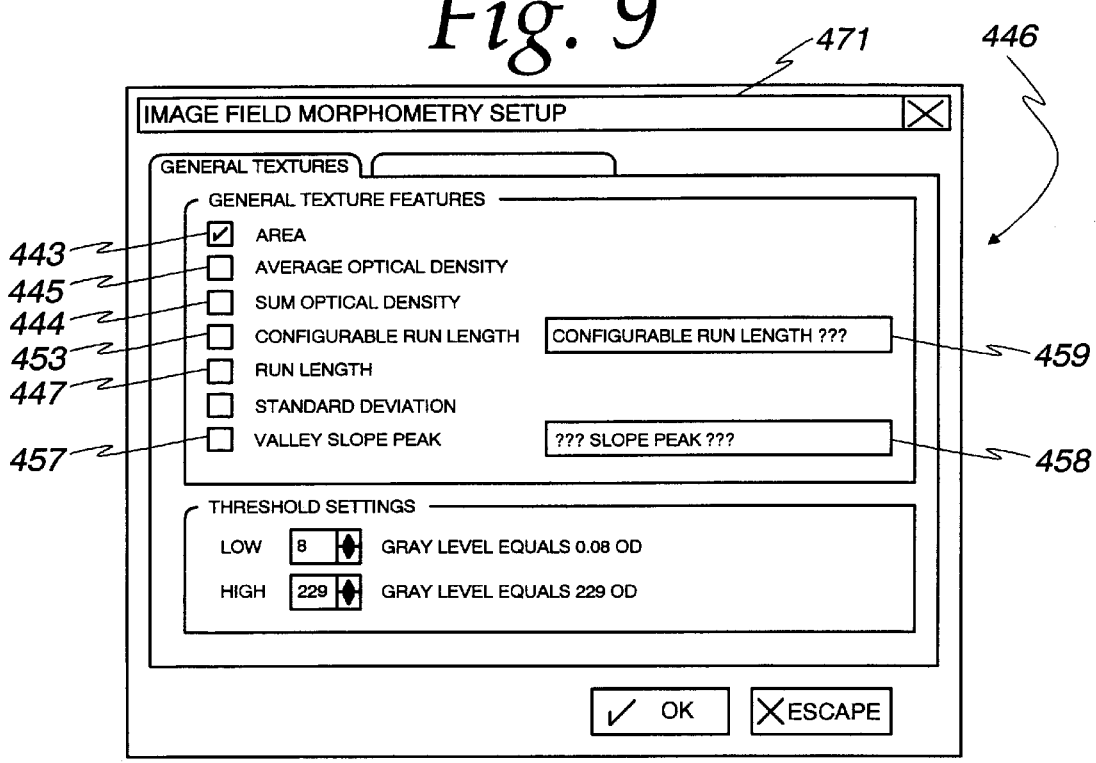
FIG. 9 shows a menu display for the selection of assays to be performed on digitized tissue samples.

After editing the displayed tissue sample, if selected, and storage of the edited image frames, analysis begins by selecting measurement from the displayed menu field 441 (FOG. 7). When measurement begins, an image field morphology page (FIG. 9) is displayed for operator interaction.

The particular analyses to be used for analysis of a given type tissue sample are selected to provide results which accurately and efficiently identify neoplastic growth. The selection of analyses is done by acquiring and analyzing many tissue samples of a given type with varying known degrees of neoplasia. The acquired image frames are then analyzed using various combinations of the tests discussed below and an assessment is made of which of the performed tests best identify neoplasia. After such "best" tests are identified for a particular tissue type, they become the standards for the identification of neoplasia in that tissue type.

At the beginning of frame analysis, the previously stored frames are individually evaluated and each pixel of the frame is compared to a predetermined threshold indicative of a meaningful value of optical density. The current value of any pixel more optically dense than the threshold is restored for that pixel and the stored optical density of any pixel which is less dense than the threshold is set to "0", representing no optical density. The comparison to the optical density threshold and setting of pixels to "0" removes potentially meaningless "clutter" from the image. Such comparison with a threshold to remove clutter may alternatively be performed prior to the image analysis operation and may be performed on the original digitized image before storage.

The particular analyses which have been identified and are used for particular tissue type analyses are discussed below, after description of the individual analyses available to the operator. The user can select at a point 443 of field 441 the measurement of the area in square microns which is a measurement of the area of non "0" optical density pixels in the recorded image. The operator can select at a point 444, the sum optical density which is the total of the density values of all pixels of the selected image frame. The average optical density can also be selected at a point 445. The average optical density is the sum optical density of all pixels in the image frame, divided by the above identified area of non-zero pixels in the frame. For each of the above analyses used, a value representing each measured quantity is stored in association with each measured image frame.

Image texture measurements are also used for analysis. For example, the measurement of run length can be selected at point 447. In the run length measurement, each non-removed frame of data, e.g. 433, is analyzed by comparing the optical density of each pixel (called the center pixel) with the optical density of both its immediate left pixel neighbor and its immediate right pixel neighbor. When the value of the center pixel is different from both neighbor pixels, the center pixel is counted and the analysis moves to the same comparison using the next pixel to the right as the center pixel. Alternatively, when the optical density of one or both of the pixels to the immediate left and right of the center pixel is the same as the center pixel, the center pixel is not counted and analysis proceeds using the pixel to the immediate right of the center pixel as a new center pixel. The analysis proceeds in raster-like rows across the frame, then down one pixel and across again until all pixels have been compared. After an entire frame of 256×256 pixels has been analyzed, the total number of counted center pixels is recorded for the frame and the process proceeds to the next image frame upon which run length is performed again. The result of the run length analysis is the total count of pixels as above counted for each frame stored for the tissue sample. Thus, if 500 frames are un length analyzed 500 counts will be stored, one being associated with each image frame.

Figure 10:
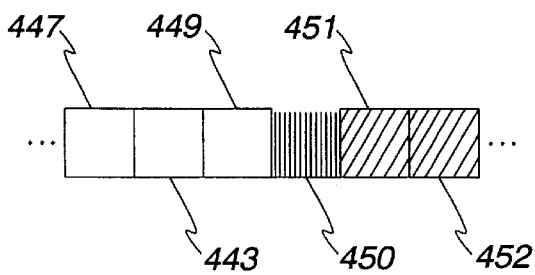
FIG. 10 shows a plurality of adjacent pixels to illustrate a run length assay.

FIG. 10, which is used to demonstrate run length analysis, represents 6 pixels 447–452 arranged in a scanned row. In the example, pixels 447, 448 and 449 are of equal optical density, pixel 450 has an optical density different from pixels 447, 448 and 449 and pixels 451 and 452 are all of an equal optical density, which is different from the optical density of pixels 447, 448, 449 and 450. When pixel 448 is the center pixel, its optical density will be compared with that of pixels 447 and 449 in the run length test. Since the optical density is the same, no count is made and pixel 449 will be next chosen as the center pixel. Since pixel 449 is of different optical density from its left and right neighbors 448 and 450, the pixel is counted and pixel 450 is next selected as the center pixel. Again, a pixel will be counted when 450 is the center pixel since its optical density is different from pixels 449 and 451; thereafter, pixel 451 becomes the center pixel. Pixel 451 is of different optical density from pixel 450, its left neighbor, but it is equal to pixel 452, its right neighbor. Accordingly, no count is made for pixel 451. As can be seen, many comparisons and pixel selections are employed to analyze an entire 256×256 pixel field.

Figure 11:
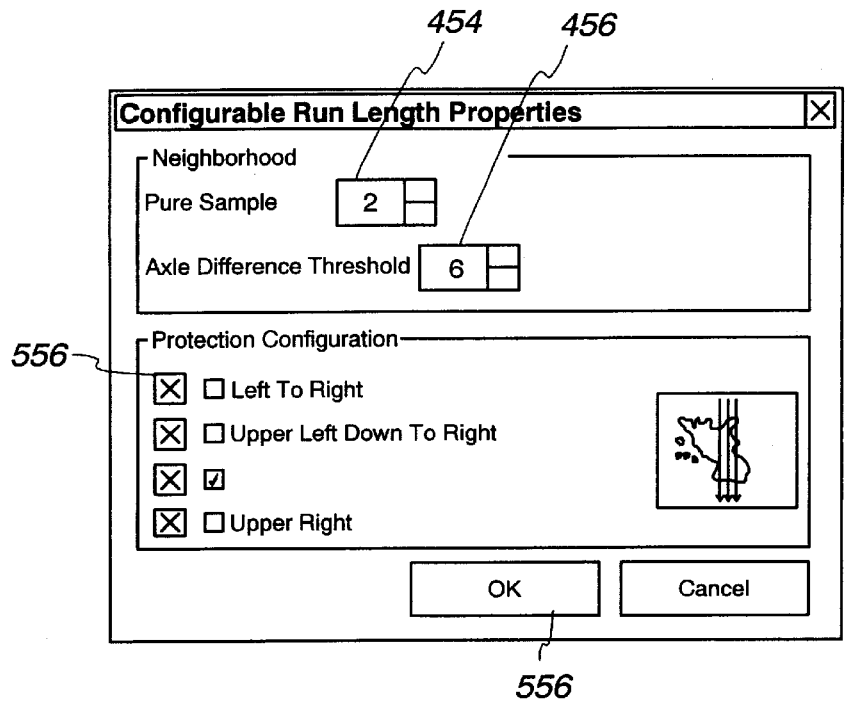
FIG. 11 shows a run length configuration setup screen with which run length analysis can be configured.

A configurable run length analysis is another available analysis option. Configurable run length is similar to run length, but the operator has more control over the comparison of pixels and the direction of center pixel selection and comparison with other pixels. Upon selecting configurable run length from the FIG. 9 menu, a new menu shown in FIG. 11 is presented to allow the user to set parameters for the analysis. Entry of a sample size value at a variable entry field 454 allows the lengthening of the comparison distance from the center pixel. For example, entering the number 2 at field 454 results in the comparison of the center pixel with its two left side neighbors and its two right side neighbors. Counting of a pixel takes place only when the conditions exist among the center pixel and the defined neighbor pixels as defined by the preset variables. A variable entry field 456 permits an operator to identify either a positive or a negative optical density difference threshold. The optical density difference threshold is the amount of optical density difference between the center pixel and a neighbor pixel which is considered the same density. When this number is positive, e.g., 0.02 OD, a center pixel will be counted when it is greater than its left and right neighbors (defined by the sample size) by an optical density of 0.02 OD or more. Similarly, when the difference threshold is negative, e.g., −0.02 OD, a center pixel is counted when it is less than its neighbors by 0.02 OD or greater.

The previously described run length analysis compares pixels in a horizontal scan row, then drops down to perform the same comparison on the next row, always comparing in a horizontal direction. The textures of various tissue types yield differing results depending on the orientation of the comparison direction. This is due in part to the shapes of the cell object of the image frame and the orientation of those cell objects. In the case of rat esophagus tissue it has been found that comparing along the general direction of the basal layer provides best results. For analysis of a tissue sample as shown in FIG. 6, top-to-bottom projection is preferred. Configurable run length permits the operator to select the comparison direction to be horizontal, vertical or at a 45° angle from upper left or upper right to provide maximum advantage. The particular direction is selected by setting one or more projection variables by selecting from four input boxes 458. After adjusting variable entry fields 454 and 456 and selecting one or more projections at 458, the operator selects an OK button 556 and returns to screen 446 of FIG. 9. The configurable run length is then performed and center pixels are counted, which compare to their neighbors in the manner defined by the variables set using the screen of FIG. 11. At the conclusion of the configurable run length analysis, a count is stored for each analyzed image frame which is the sum of all center pixels meeting the tests established by the variables. When more than one projection is selected, the result of configurable run length analysis is the sum of all counted pixels for all projections.

Figure 12:
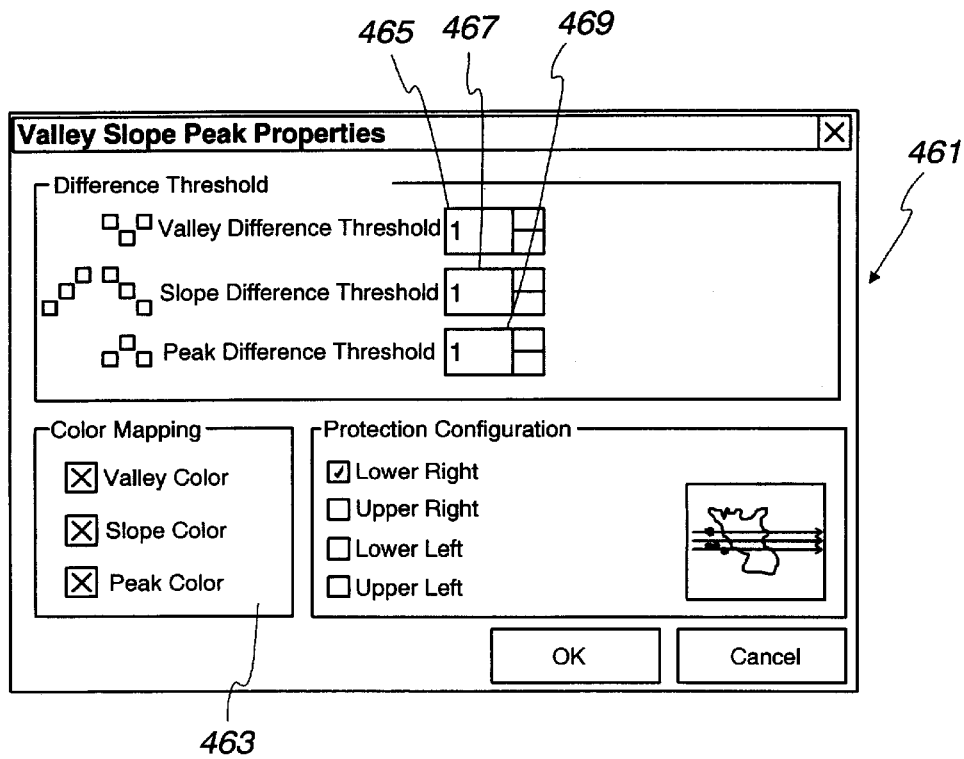
FIG. 12 shows a valley-slope-peak setup screen.

Another texture analysis called valley-slope-peak can be selected to analyze the image frames of tissue samples. As with the preceding analyses, variables are adjusted to define this analysis. Upon selection of valley-slope-peak a variable setting menu 461 (FIG. 12) is presented to the operator to define the analysis variables. In valley-slope-peak, a center pixel is compared with its immediate neighbor pixels in a direction selected at projection configuration 463. The available directions are left to right, upper left to lower right, top to bottom and upper right to lower left. When a center pixel is less than both of its adjacent neighbor pixels by an amount equal to or greater than a valley difference threshold set at point 465, the center pixel is counted as a valley pixel. When a center pixel is less than the neighbor pixel to one side and greater than the neighbor pixel on the other side, by an amount selected at a slope difference threshold 467, the center pixel is counted as a slope pixel. Lastly, when the optical density of a center pixel is greater than both neighbor pixels by a peak difference threshold set at 469, the center pixel is counted as a peak pixel. As with the run length measurement, all pixels of a field are selected in the predetermined direction for the valley-slope-peak tests and the various valley-slope-peak pixel counts are retained on a per-image frame basis as indicative of the texture of the image field. After a frame is analyzed, the process proceeds to valley-slope-peak analysis of another image frame until all image frames of the sample are analyzed and all valley, slopes and peaks have been counted and results recorded.

The valley-slope-peak counts are also used to define a result called coarseness which is defined as the slope count minus two times the peak count-valley count [Consensus= slope-2 (peak-valley)]. When the operator selects the coarseness results, valley-slope-peak analysis is performed and at the conclusion of each image frame analysis, the coarseness is calculated from the valley, slope and peak counts from that image frame. A coarseness results is stored in association with each analyzed iamge frame.

Figure 13:
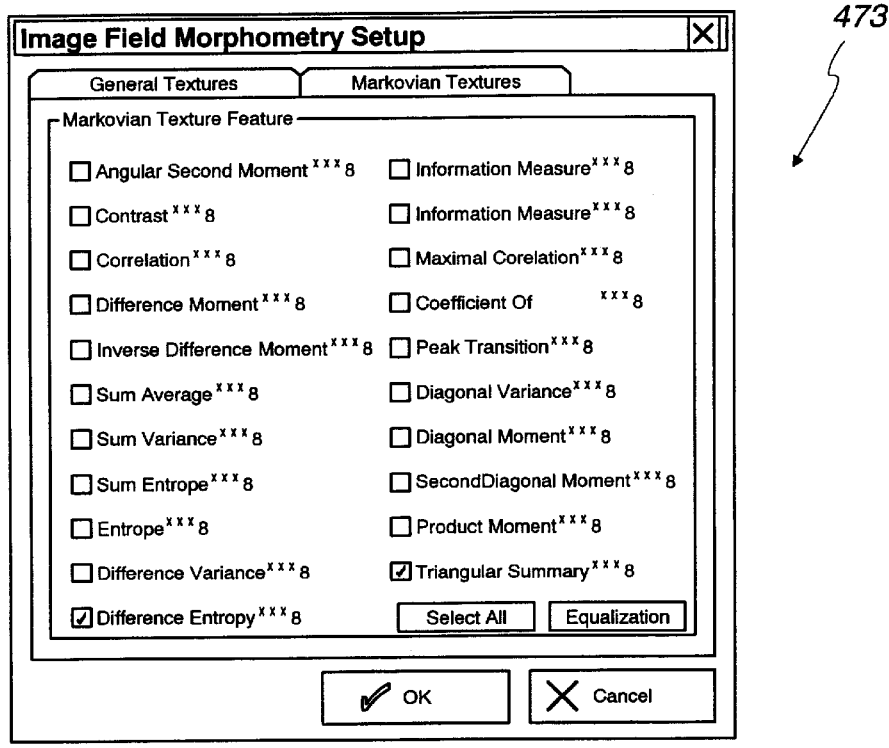
FIG. 13 shows a Markovian Texture analysis setup screen.

Markovian texture analysis can be also selected as an image field texture analysis of the tissue selection. The selection of Markovian textures on screen 446 causes a variable setting screen 473 (FIG. 13) to be presented to the operator. Screen 446 permits the operator to select up to 21 of the known Markovian texture analyses and to set variables to refine the selected analyses. The performance of the individual Markovian analyses is described in detail in the literature, such as Pressman, NJ: "Markovian analysis of cervical cell images", J. Histochem Cytochem 24:138–144, 1976. In Markovian analysis, a histogram of 8 grey ranges is created to count the optical density of pixels. The common technique for identifying the 8 grey level ranges, as described in the above Pressman article, is called floating equalization in which the pixels having the least and most optical density are first identified and the range between them is divided into 8 equal grey level ranges. The floating equalization brings out the texture of the analyzed sample but the actual optical density information is lost. The present Markovian analysis allows the operator to select a fixed equalization process and to define the upper and lower boundaries of the fixed equalization range. As before, the fixed range is divided into 8 equal sized grey level ranges for an optical density counting histogram. The fixed equalization provides the usual results from Markovian analyses but the actual optical density information is preserved. Additionally, the operator can adjust the step size of the performed Markovian analysis.

EXAMPLES

The preceding has described the apparatus used to acquire and digitize image frames of tissue samples, how image frames are edited and stored, and the types of analyses available to identify neoplasia. The following sets forth examples for the use of these tools in identifying neoplasia and using such identification to test possible chemopreventive agents and diagnosing possible cancers.

One manner of testing chemopreventive agents uses rats which are treated with a carcinogen to develop a particular neoplastic growth and ultimately a carcinoma. A first group of the rats is treated with a carcinogen, and a second group is then treated with the same carcinogen and also with an expected chemopreventive agent while a third control group is not treated in any way. The effectiveness of the administered chemopreventive agents can then be evaluated by comparing the progression of neoplasia in the two treated groups versus the control group. The experiment is designed to sacrifice groups of animals at various time periods to assess neoplastic development. The present analysis permits early detection of the pre-cancerous conditions, which greatly shortens the time required to assess the effectiveness of chemopreventive agents. Shortening the times is important because there are many compounds to test and shorter, more precise testing saves testing costs and identifies chemopreventive agents for possible use earlier than other analysis methods, such as human visual tissue inspection or time to death from cancer or survival rates.

The present analysis is also used to evaluate tissue samples of animals, including humans, for possible neoplasia, which can result in an early diagnosis of pre-cancerous conditions and can thus greatly increase patient survival rates over later detection, possibly after metastasis. The present analysis has been used to analyze human cervix tissue samples to identify the extent of progression of early pre-cancerous conditions.

The first example relates to the analysis of rat esophagus tissue for the growth of neoplasia and the use of detected neoplasia in the identification of chemopreventive agents.

Figure 22A:
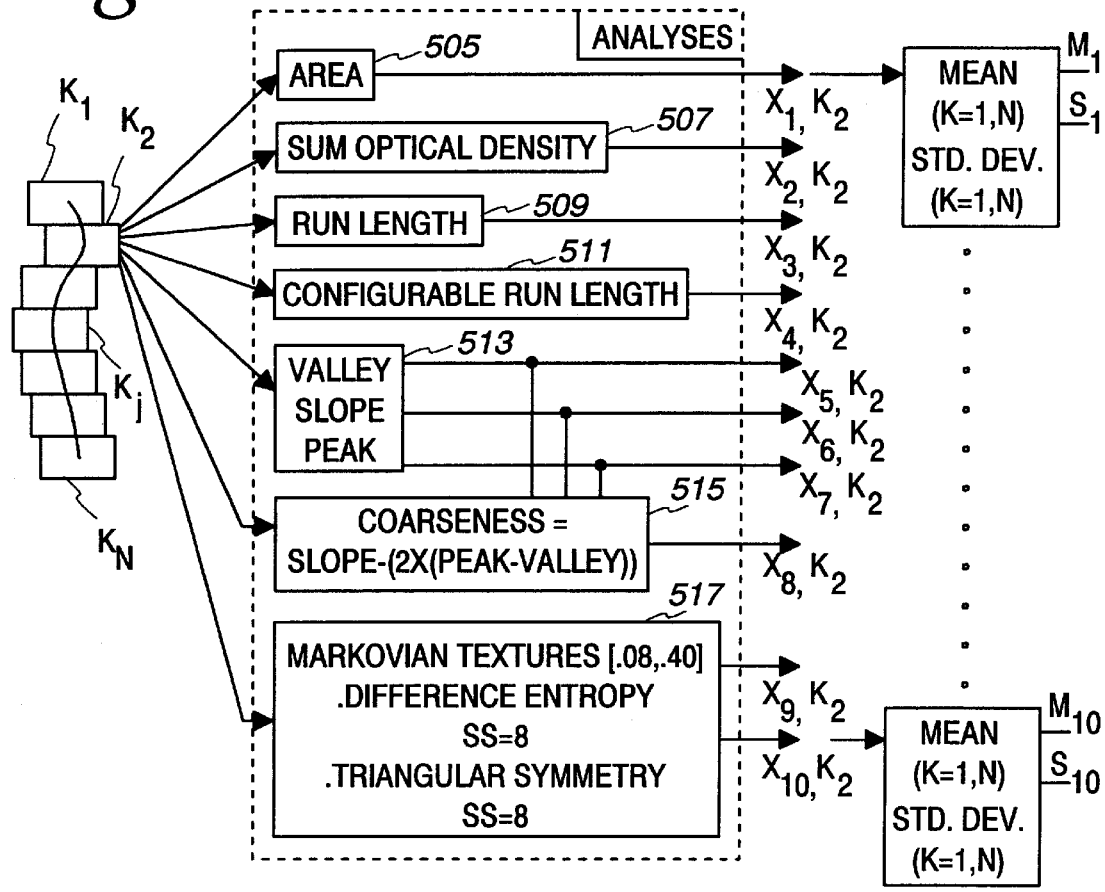
FIGS. 22A–B illustrate an analysis example performed on rat esophagus tissue sections.
Figure 22B:
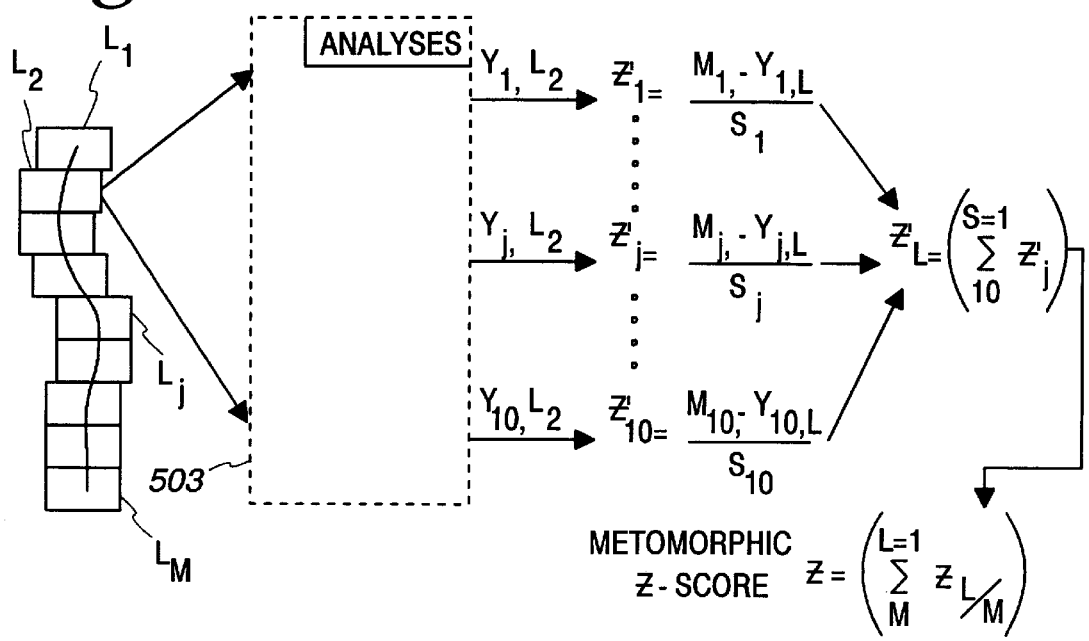

FIGS. 22A and 22B comprise a diagrammatic representation of the analysis of rat esophagus tissue. FIG. 22A includes a representation of a plurality of image frames $K_1$ through $K_N$ acquired from a normal rat esophagus tissue sample 501. A dotted line box 503 labeled analyses is shown connected by illustrative arrows 502 to receive image data from image frame $K_2$. In the example, the analyses 503 are sequentially connected to receive stored image frame data from all image frames $K_1$ through $K_N$. The particular analyses shown in box 503 and discussed herein have been selected after detailed study to have significant value in the detection of neoplasia in rat esophagus tissue. After the analyses have been selected for use on a particular tissue type, such as rat esophagus, they become the standard for testing that tissue type.

As previously described, the best results from the varied analyses performed are achieved when they are reported as a morphometric Z-score. The morphometric Z-score is a normalizing of the results which uses a mean and standard deviation of analyses performed on normal tissue. The analysis of normal tissue should be done using the same analyses as are to be used for the analysis of neoplasia in suspected tissue. Determining the mean and standard deviation from normal tissue is not a sequential step of each analysis but it is to be performed before the results of the analysis of suspected tissue are normalized. Accordingly, for a given set of analyses the evaluation of normal tissue can occur once and the result stored as a library for later use in normalizing results of suspected tissue.

Each image frame, e.g., $K_2$, is evaluated by each of the 10 analyses 505–517 shown within the analyses box 503, then the evaluation proceeds to perform the analyses on the next image frame. Each analysis, such as area analysis 505, of an image frame results in a result $X_1, K_2$ for that analysis and that image frame.

The tests performed on each image frame of the tissue sample begin with Area 503, sum optical density 507 and run length 509 which are performed as previously described. A configurable run length 511 is also performed on each image frame. The configurable run length analysis for rat esophagus tissue has a step size of 1 pixel, a difference threshold of −0.60 OD and a projection from top to bottom. A valley-slope-peak analysis 513 is also performed and 3 analysis results $X_5, K_2$; $X_6, K_2$ and $X_7, K_2$ for the valley count, slope count and peak count, respectively. For the valley-slope-peak analysis the difference threshold is set to 0.01 OD and the projection is from left to right for all tests. In addition, an overall threshold of low=0.08 OD to high= 0.229 OD is set. The results of the valley-slope-peak analysis are separately stored for later use and are also combined into a coarseness measurement by analysis 515. Finally, the Markovian texture analyses of difference entropy $X_9,K_2$ and triangular symmetry $X_{10},K_2$ are performed. Both Markovian analyses use a step size of 8 pixels and a fixed equalization between 0.08 OD and 0.4 OD At the conclusion of the analyses 503 of the normal tissue sample, a set of 10 test results $X_1,K_N$ through $X_{10},K_N$ exists for each of the N image frames analyzed. When, for example, 300 image frames are analyzed, this yields 300 results for each of the tests 505–517.

After all analyses have been completed on the normal tissue section 501 image frames, the mean M and standard deviation S must be calculated for each analysis for later use in normalizing the results gained from analysis of suspected neoplastic tissue. In FIG. 22A the normal tissue mean and standard deviation for the area analysis are shown as $M_1$ and $S_1$, respectively, and the mean and standard deviation for the triangular symmetry Markovian analysis are shown as $M_{10}$ and $S_{10}$, respectively.

FIG. 22B represents the analysis of a suspected neoplastic rate esophagus tissue section represented at 527 and having a plurality of acquired image frames $L_1$ through $L_M$. As previously described, the image frames are acquired and digitized and they are then analyzed using the same 10 analyses 505–517 shown in FIG. 22A and having the same variable settings. The results of these analyses are shown as $Y_1,L_2$ through $Y_{10},L_2$ for the second image frame $L_2$. When the results of all 10 analyses $Y_1,L_2$ through $Y_{10},L_2$ have been computed and are stored in association with a respective image frame, they are normalized using the mean M and standard deviation S computed for corresponding analysis of the normal tissue sample 501. More specifically, the results of the area analysis 505 for suspected neoplastic tissue yields a result $Y_1,L_2$ for the second image frame $L_2$. The result is converted to a preliminary Z-score ($Z'_1$) by subtracting $Y_1,L_2$ from the mean $M_1$ identified for normal tissue and dividing the result by the standard deviation $S_1$ of the normal sample. Similarly, each test result is subtracted from the corresponding mean $M_1$ through $M_{10}$ and the result divided by the respective standard deviation $S_1$ through $S_{10}$ of normal tissue. Preliminary normalizing creates 10 values, $Z'$ through $Z'_{10}$, one for each different test performed on the same image frame. The 10 Z' values are averaged to result in the Z-score $Z_i$ for the image frame. After a value $Z_i$ has been determined for each image frame, all of the image frame Z-scores $Z_i$ are averaged to yield an overall Z-score for the tissue sample. This resulting Z-score can be accurately compared with the Z-scores of other tests, whether or not the tests were performed on the same tissue type.

Figure 15:
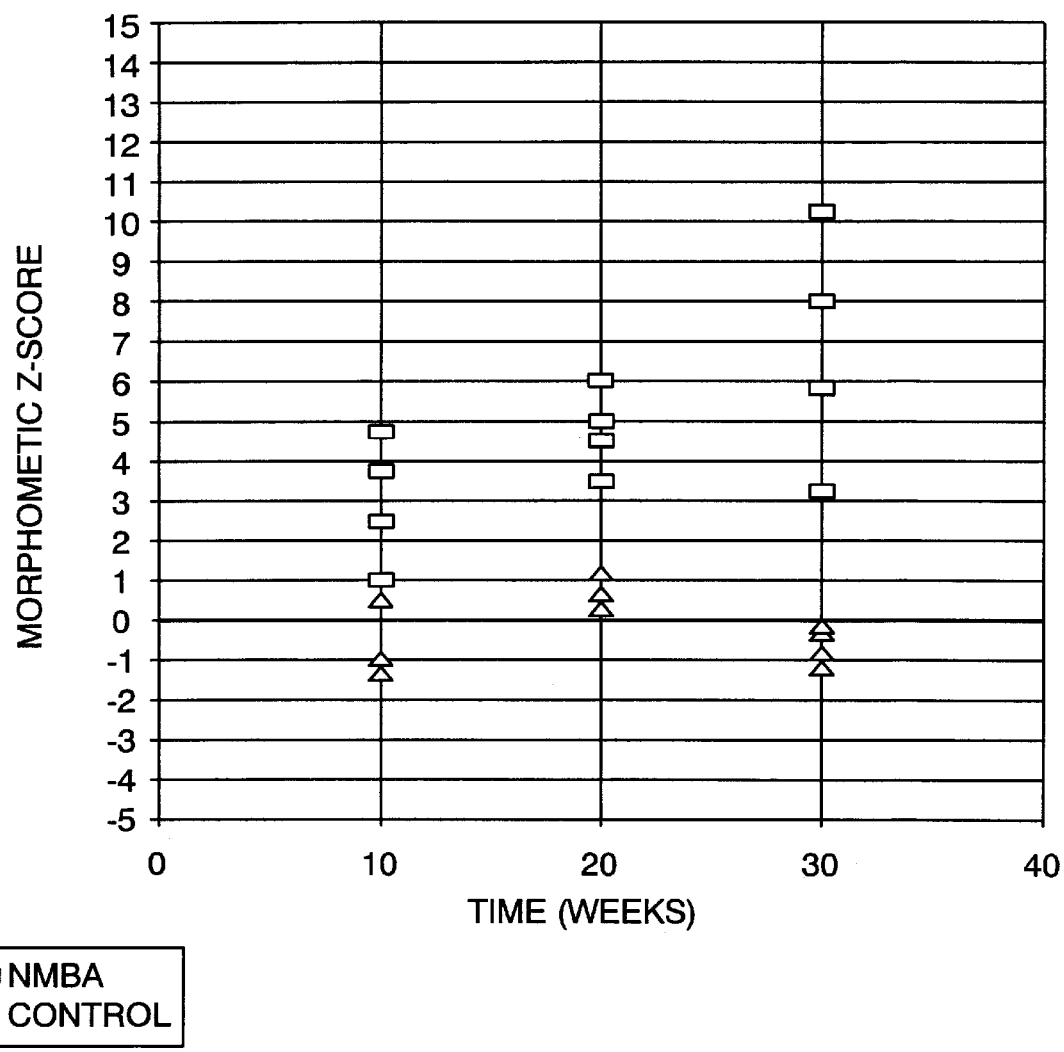
FIG. 15 is a graph of average Z-scores measured from tissue sections taken from experimental animals over a period of 30 weeks.

FIG. 15 is a graph comparing the increasing Z-scores over time of esophagus tissue of rats induced by treatment with N-Nitrosomethylbenzlamine (NMBA) which causes neoplasia compared to a control population which was not treated with NMBA. At ten weeks into the trial the Z-score of the normal population ranges from +0.5 to −1.5, while the Z-score of the esophagus tissue in NMBD-treated animals exhibiting neoplasia ranges from +1.0 to +4.5. At 20 weeks the control population exhibits a Z-score between 0 and 1, while the tissue from the esophagus of treated animals exhibits a Z-score from +3.5 to +6. At 30 weeks the control tissue exhibits a Z-score from 0 to −1.5, while the tested tissues exhibit a Z-score of +3.5 to +10.5. From FIG. 15 it is apparent that the tests performed show a substantial departure from the control group as early as 10 weeks into the trial, which departure increases markedly at 20 and 30 weeks.

Figure 14:
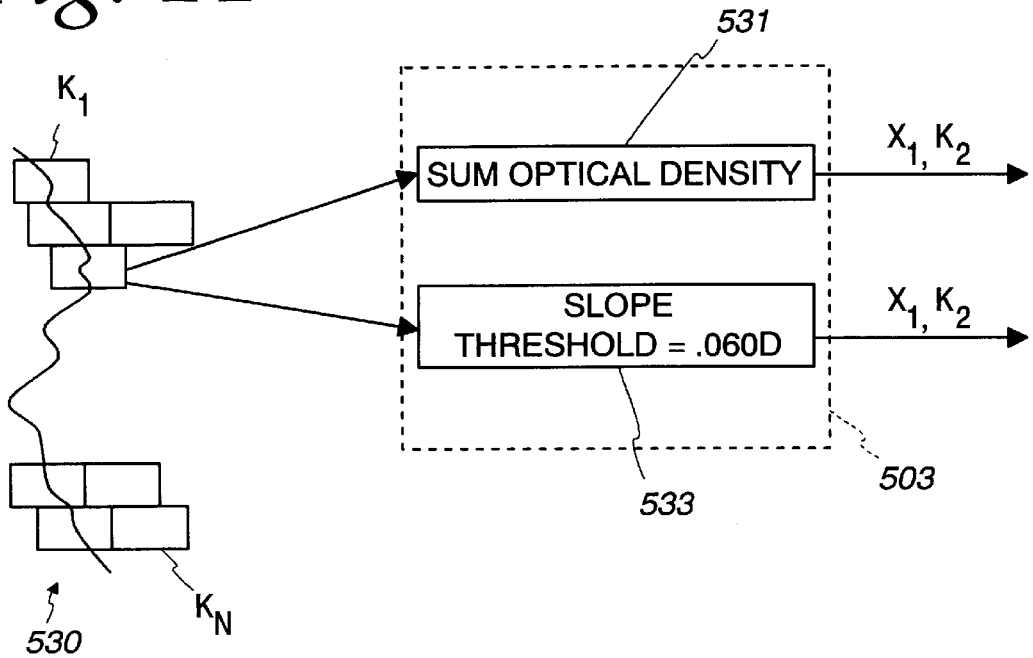
FIG. 14 shows the set of analyses used to evaluate human cervix tissue samples.

FIG. 14 represents the analyses performed to detect neoplasia in human cervix tissue samples represented at 530. As discussed with regard to rat esophagus tissue, a set of analyses 503 useful in detecting neoplasia is performed on normal tissue samples and on suspected neoplastic tissue sections. For human cervix tissue a sum optical density 531 analysis and the slope test 533 make up the set. The slope analysis is performed with a difference threshold of 0.06 OD and projections in the direction of all 8 pixel neighbors. Both analyses are performed on normal tissue and a mean M and a standard deviation S is computed for each test. The same set of analyses are then performed on tissue suspected to exhibit neoplasia. The analysis results of the suspected tissue are then normalized in the manner of the rat esophagus tissue and the resulting Z-score is used to represent the tissue sample.

Figure 16:
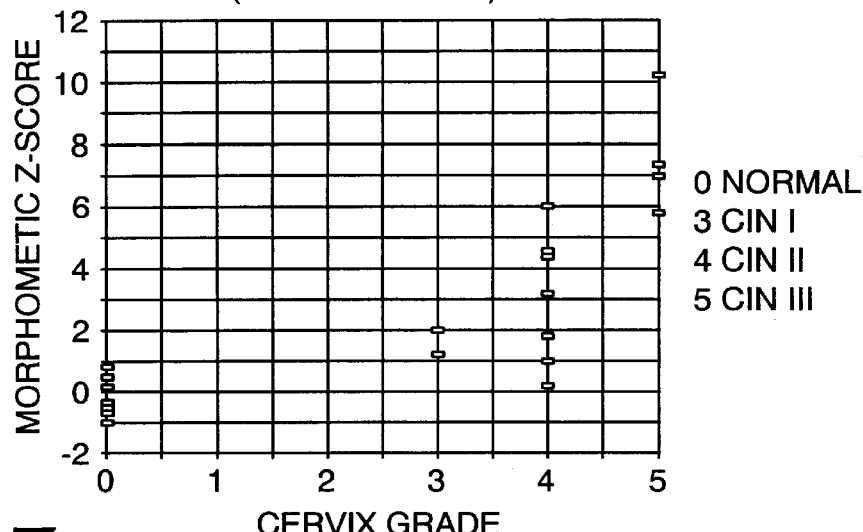
FIG. 16 is a graph of the correlation of Z-scores of human cervical tissue sections having known levels of neoplasia, compared to normal.

FIG. 16 is a graph of Z-scores obtained by analysis, in accordance with the preferred embodiment, of human cervix tissue sections identified by pathology experts to be in progressive stages of neoplasia ranging from normal tissue through cervical intraepithelial neoplasia grade III (CIN III). In FIG. 16, the Z-scores of normal tissue range from −1 to +1. The Z-scores of tissue of CIN I range from +1 to +2; the Z-scores of tissue of CIN II range from 0 to +6 and; the Z-scores of tissue of CIN III range from +5.5 to +10. Clearly the apparatus and methods of the present embodiment shown increasing Z-scores for increasing neoplasia.

Figure 23:
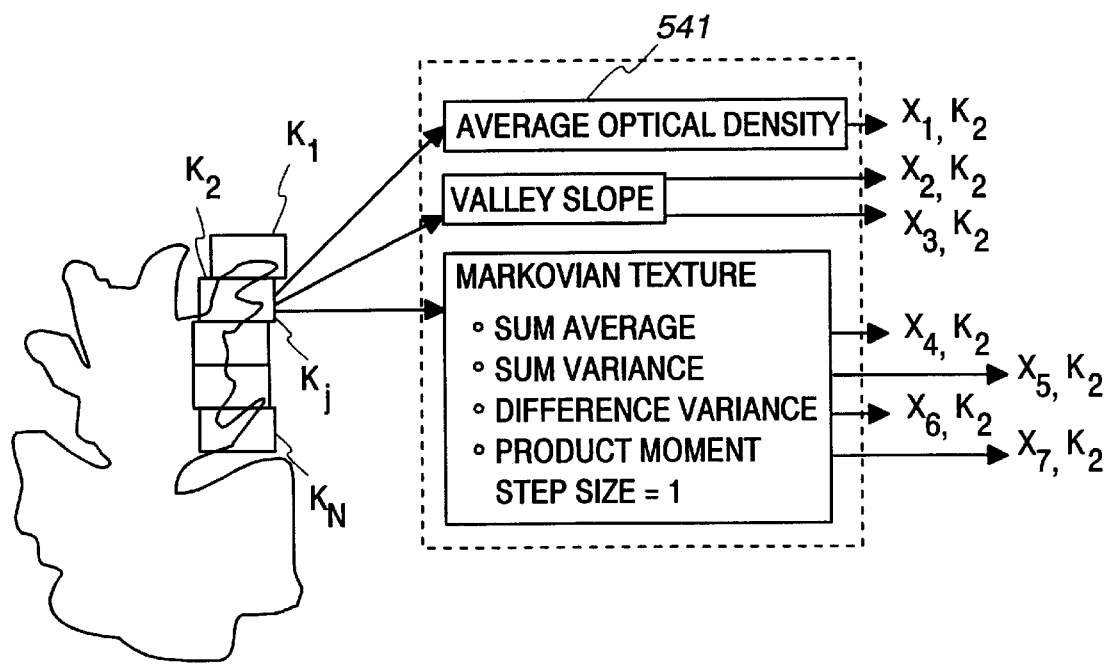
FIG. 23 illustrates an analysis example performed on rat colon tissue sections.

FIG. 23 represents the analyses performed to detect neoplasia in mouse colon tissue sections represented at 540. The analyses 503 performed on mouse colon tissue consist of average optical density, valley and slope and the Markovian textures of sum average, sum variance, difference variance and product moment. The valley and slope analyses are each performed with a difference threshold of 0.01 OD and in all projections. The Markovian textures analyses are all performed with a step size of 1 pixel and a fixed equalization between the values 0.08 OD and 0.70 OD.

Figure 18:
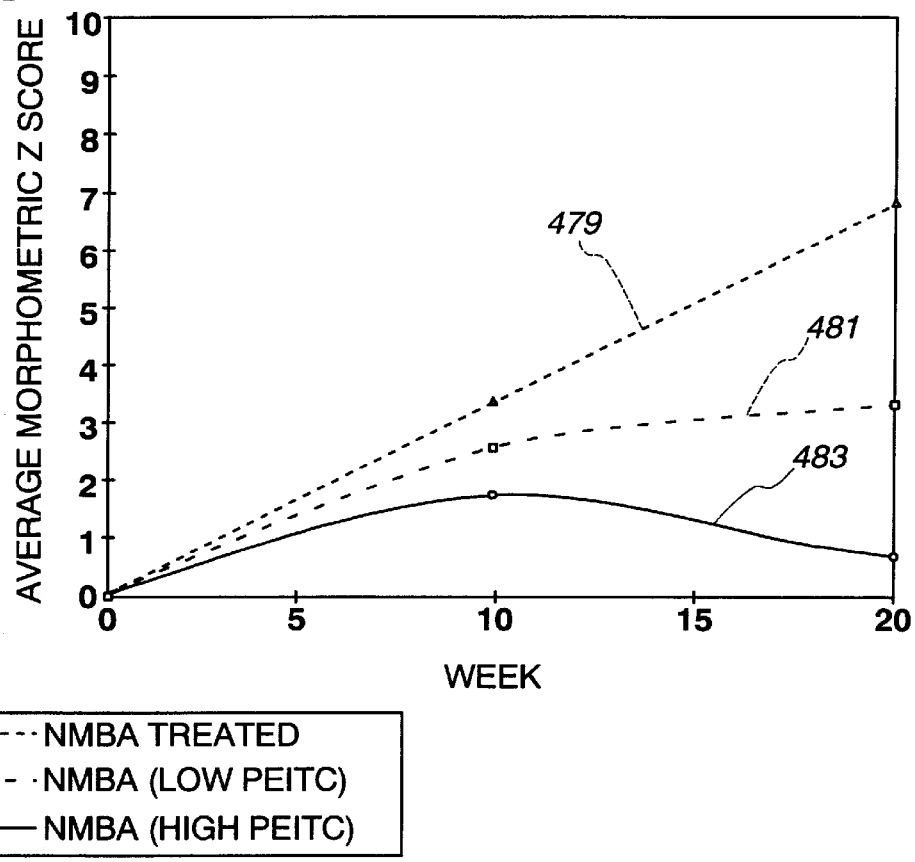
FIG. 18 shows the Z-scores of tissue sections from experimental animals given different levels of chemopreventive agents.

The efficacy of the present embodiment in identifying chemopreventive agents is shown in the graph of FIG. 18. The results of testing three groups of rats for neoplasia in accordance with the present embodiment show differences in the group results based on dosage of phenethylisothiocyate (PEITC), a likely chemopreventive agent. All groups were treated with NMSA in a manner to produce a likelihood of neoplasia, similarly to the groups shown in FIG. 15. The first group, shown by line 479, received no PEITC during the test and the result is a nearly straight projected line for an average Z-score of 0 at the inception of the test to an average Z-score of almost 7 at 20 weeks into the test. The second group (line 481) which received low doses of PEITC, exhibit an average Z-score of approximately +2.5 at 10 weeks and an average S-score of approximately +3.25 at 20 weeks. The third group (line 483) which received a high dosage of PEITC exhibits an average Z-score of approximately +1.5 at 10 weeks and a reduction in Z-score to approximately +0.75 at 20 weeks.

Figure 19A:
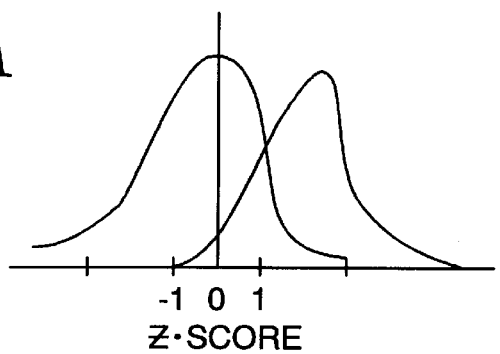
FIGS. 19A–B show a before and after distribution of one group of the experimental animal tissues of FIG. 18.
Figure 19B:
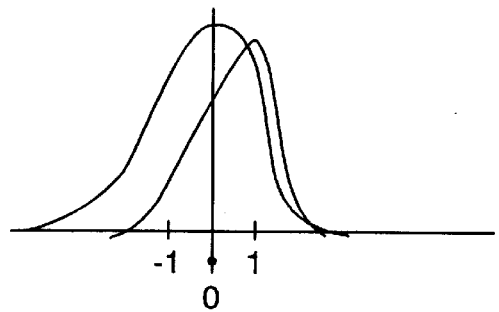

The test results can also be presented in a manner referred to an "with and without treatment" or "before and after" as shown in FIGS. 19A–B. FIG. 19A shows the "without" or "before" image of test results measured at 10 weeks after administration of a high dosage of NMBA without PEITC (line 479 of FIG. 18) and FIG. 19B shows the "with" or "after" image of test results measured at 10 weeks after administration of a high dosage of PEITC. The movement of the measured distribution closer to the mean as is already demonstrated by FIGS. 19A–B shows the improvements achieved by the use of the chemopreventive agent PEITC.

In the above described embodiments, the analysis and computation of the Z-scores are performed by the computer 32 (FIG. 2) of the image analysis equipment. It should be mentioned that the accumulated image frame data may be stored on removable media or made available on a network, and the analysis and computation of the Z-scores may be performed on another computer system. That is, the analysis need not be performed by the data acquisition computer system. As an example, the image frame data may be collected on a first computer and interactively analyzed by an operator at a second computer. The operator may select fields individually, rather than by a scanning method. This may be desirable for small, hard to locate, neoplasia lesions such as prostate interephithelial neoplasia (PIN) lesions, where accumulation of results may occur at many distinct sites.

Figure 17:
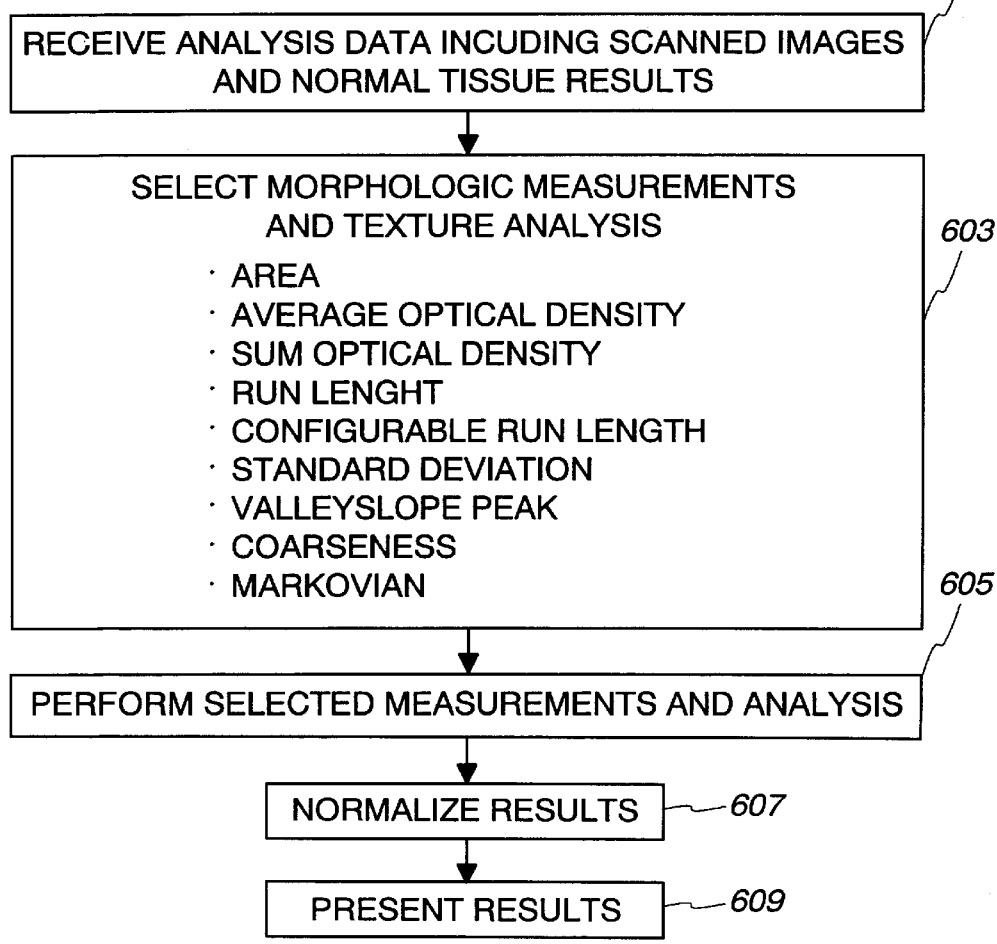
FIG. 17 is a flow diagram of the function performed by the scanning and analysis apparatus.

FIG. 17 shows the functions of the analysis apparatus. In a block 601 the analysis data is received by the apparatus. The analysis data includes the digitized image frames as well as the results of the analysis of "normal" tissue samples. The digitized image frame may be already be stored in the apparatus when the analysis apparatus is also the scanning apparatus, or the digitized images may be received from movable storage media or downloaded from a network. The analysis results from normal tissue may be entered from movable media or the keyboard 56.

Block 603 represents the selection of analyses by an operator, as represented in display screens 9, 11, 12 and 13 ad discussed above. After the selections of analyses, the apparatus, block 605, performs the requested analyses in the manner discussed above and the results are stored in the apparatus. At the conclusion of measurements and analyses, the apparatus reads the stored results and the results for normal tissue and computes the Z-scores in block 607, as discussed with regard to FIGS. 14, 22A, 22B and 23. The results of measurements and analyses, including the Z-scores computed by the apparatus, are then presented to the operator in block 609. Examples of such presented results are shown, for example, in FIGS. 15, 16 and 18. The results can also be stored for digital presentation on movable media or via a network. The preceding description sets forth analysis apparatus and methods for use in identifying the development of preinvasive neoplasia. Also described are methods for evaluating possible chemopreventive agents and the use of the disclosed methods and apparatus in such evaluating. The present invention is not limited to the above embodiments but extends to cover other embodiments, not shown or described, but falling within the ambit of the appended claims.

What is claimed is:

1. A method of analyzing a tissue sample having a layer of adjacent, connected tissue cells for pre-invasive neoplasia, comprising:

optically and microscopically scanning the tissue sample having adjacent, connected tissue cells to provide, multiple image fields and electronically recording these image fields to provide spatially adjacent multiple image fields of the tissue sample larger than a single view of the adjacent, connected tissue cells;

forming a reconstituted image of the suspected neoplasia tissue from the multiple, electronically recorded, spatially adjacent image fields larger than a single field of view and having adjacent connected tissue cells in the reconstituted image;

displaying to the viewer the reconstituted tissue image comprised of multiple, spatially adjacent image fields larger than a single field of view;

determining and selecting from the reconstituted, tissue image a region of adjacent connected tissue cells for analysis at a resolution; and analyzing tissue sample images of the selected region at the resolution for the analysis of pre-invasive neoplasia.

2. A method in accordance with claim 1 wherein the step of analyzing the selected region includes:

measuring morphometric features of tissue sample images in first unit values;

measuring texture features of tissue sample images in other units or scale values; and combining the measured units and scale values into a common scale.

3. A method in accordance with claim 1 wherein the step of analyzing the selected region includes:

optically and microscopically scanning normal tissue samples and analyzing these normal tissue samples using a combination of morphometric and texture measurements; and optically and microscopically scanning abnormal tissue samples and analyzing these abnormal tissue samples using the same combination of morphometric and texture measurements as used for the normal tissue.

4. A method in accordance with claim 3 including the steps of:

determining the mean and standard deviation for the measurements of the normal tissue; and subtracting the mean for normal tissue measurements from the abnormal tissue measurements and dividing by the normal tissue's standard deviation to provide a morphometric score.

5. A method in accordance with claim 4 including wherein the recording step comprises recording the morphometric scores on a graph with a morphometric scale on the ordinate and a time scale on the abscissa to illustrate any progression of neoplasia.

6. A method in accordance with claim 1 wherein the tissue includes a basal layer of tissue cells and the analysis is for neoplasia, said method including the steps of:

addressing a plurality of the tissue sample images adjacent the basal layer;

orienting the addressed tissue sample images to form a tiled, combined, reconstituted image of a portion of the scanned tissue sample; and the determining and selecting step comprises editing the reconstituted image of the basal layer to delete portions thereof from the subsequent analysis.

7. A method in accordance with claim 6 including the steps of:

scanning the tissue sample at a first magnification resolution; and decreasing the resolution for the reconstituted image.

8. A method in accordance with claim 7 including the steps of:
   interactively viewing the recorded tissue sample images; and
   interactively editing to leave substantially only the basal layer of cells and cells evolving therefrom.

9. A method in accordance with claim 6 wherein the editing step comprises:
   displaying a tissue sample image selected from the reconstituted image at a higher resolution than the reconstituted image; and
   erasing from the displayed tissue sample image, one or more portions thereof having limited analysis value.

10. A method in accordance with claim 9 comprising replacing the selected image of the reconstituted image with the edited version of the selected tissue sample image.

11. A method in accordance with claim 1 including the step of selecting, from a menu of measurements, a first set of morphometric and texture measurements which are highly discriminating for a first kind of tissue sample; and
   selecting a second set of different morphometric and texture measurements which are highly discriminating for a second kind of tissue sample.

12. A method in accordance with claim 1 wherein the analyzing step comprises analyzing a tissue sample image for a predetermined texture feature and the method comprises:
   identifying a mean value of the result of analyzing normal tissue images for the texture feature;
   determining the mean value of the result of analyzing the tissue sample image for the predetermined texture feature;
   subtracting the mean value identified for the particular texture feature of normal tissue from the mean value determined for the particular texture feature of the analyzed tissue sample image; and
   recording the result of the subtracting step.

13. A method in accordance with claim 12 comprising identifying the standard deviation of the results of analyzing normal tissue images for the predetermined texture feature and dividing the result of the subtraction step by the identified standard deviation.

14. A method of claim 1 comprising presenting the recorded results in a manner which normalizes the results of different analyses.

15. A method of analysis of a tissue sample having adjacent, connected tissue cells comprising the steps of:
   optically and mircroscopically scanning the tissue sample to provide multiple tissue sample images having adjacent, connected tissue cells therein, and electronically recording the tissue sample images to provide multiple tissue sample images of the tissue sample;
   reassembling the recorded tissue sample images to form a reconstituted, tissue sample image comprised of multiple spatially adjacent, microscopic, tissue sample images from the tissue sample;
   measuring sections of the reconstituted tissue sample image with respect to area;
   measuring sections of the reconstituted tissue sample image with respect to optical density;
   measuring the morphological texture of adjacent, connected tissue cells of sections of the reconstituted tissue sample image;
   analyzing the results of the measured area, optical densities and morphological texture of adjacent, connected tissue cells of the selected sections of the reconstituted tissue sample image of adjacent, connected tissue cells to provide morphological data; and
   providing the morphological data for an analysis of the reconstituted tissue sample image of adjacent, connected tissue cells.

16. A method of analysis in accordance with claim 15 wherein the step of analyzing the texture of the tissue sample image comprises the step of measuring run length which includes an analysis of neighboring cells in the tissue sample image for optical densities above a predetermined threshold.

17. A method of analysis in accordance with claim 16 wherein the tissue sample has a basal layer extending in a given direction; and
   making the run length configurable by analyzing neighboring cells in the given direction of the basal layer.

18. A method in accordance with claim 15 wherein the texture measuring step comprises making at least one of a valley, slope or peak measurement.

19. A method in accordance with claim 18 wherein a coarseness measurement of the texture is obtained by subtracting from the slope measurements, the peak and valley measurements.

20. A method in accordance with claim 15 wherein the texture measuring step comprises the making of a Markovian Texture measurement.

21. A method in accordance with claim 20 including the steps of analysis of human cervix tissue sample images wherein the step of measuring morphological texture includes the making of Markovian Texture measurements.

22. A method of analyzing a basal layer sample of tissue having adjacent, connected tissue cells evolving from the basal layer for neoplasia, said method comprising the steps of:
   optically and microscopically scanning the adjacent, connected tissue cells along the basal layer over a plurality of tissue sample fields to provide microscopic, multiple spatially adjacent, image fields of the tissue sample;
   recording these image fields and reassembling these image fields to form a reconstituted, magnified image comprised of multiple image fields of the tissue and having the basal layer thereon;
   tracing the basal layer for analysis;
   analyzing the traced basal layer of the reconstituted tissue sample image with respect to area and optical density;
   analyzing the traced basal layer of the reconstituted tissue sample image with respect to texture by making measurements including the step of an analysis of texture by examining adjacent, neighboring cell images with respect to values above or below a predetermined threshold; and
   providing the texture analysis of adjacent, connected tissue cells for use in evaluation of neoplasia.

23. A method in accordance with claim 22 including the step of configuring the run length to extend in the direction that the basal layer extends.

24. A method in accordance with claim 22 including the step of analyzing adjacent tissue cells to provide at least one of valley, slope and peak measurements.

25. A method in accordance with claim 22 including the step of measuring the tissue cell images using a Markovian Texture analysis.

26. A method in accordance with claim 22 for analysis of human cervix tissue including the steps of:
   measuring the summed optical densities from the cervix tissue cell images; and measuring the slope between adjacent human cervix cell images.

27. A method in accordance with claim 22 including the steps of:
  analyzing an animal tissue to provide discriminating data comprising the steps of:
  measuring the average optical densities of the animal tissue cell images;
  measuring the valley and slope from adjacent cell images of the animal tissue; and
  measuring Markovian Textures of the animal cell images.

28. A method in accordance with claim 22 wherein the texture measurements of animal tissue includes using at least one of the following steps:
  measuring the run length of adjacent animal tissue cell images;
  measuring the run length which is configured in direction and the spacing between analyzed cell images;
  measuring the valley, slope and peak between adjacent cell images;
  measuring the coarseness which includes the step of subtracting the peak and valley from the slope; and
  measuring Markovian Textures of the analyzed cell images.

29. A method in accordance with claim 22 including the step of recording the results of the respective measurements in a manner which normalizes the results of the morphometric and texture analyses.

30. A method of analyzing histological tissue samples of different kinds of tissues having adjacent connected tissue cells having inherent variabilities for pre-invasive cancer comprising the steps of:
  for each of the histological tissue samples, optically scanning the tissue sample at a plurality of non-overlapping tissue sample fields and electronically recording a high resolution tissue sample image representing selected fields for each of the different kinds of tissues;
  analyzing each of the respective tissue sample images using a combination of morphometric and texture analyses of histological tissue predetermined to be indicative of the progression of cancer development for each of the kinds of tissues;
  normalizing results of selected analyses performed in the analyzing step for the respective kinds of tissues to a common standard; and
  deriving values for the respective kinds of tissues so that a comparison can be made indicative of the progression of their respective cancer developments from the normalized results.

31. A method in accordance with claim 30 including the step of editing the recorded tissue sample images to delete portions of the image not representing the basal layer and the evolving tissue cells to create edited tissue sample images and wherein the analyzing step comprises analyzing the edited tissue sample images.

32. A method of analyzing the efficacy of a chemopreventive agent on first and second precancerous tissues of adjacent, connected tissue cells, said method comprising the steps of:
  optically and microscopically scanning the first precancerous tissue to provide image fields and electronically recording the image fields to provide multiple image fields of the first precancerous tissue; integrating the recorded image fields into a reconstituted, first tissue sample image comprised of multiple image fields representing the first tissue;
  analyzing tissue regions of the first reconstituted tissue sample image using a first set of morphometric and texture features highly discriminating for the first precancerous tissue;
  optically and microscopically scanning the second precancerous tissue to provide image fields and electronically recording the image fields to provide multiple image fields of the second precancerous tissue; integrating the recorded image fields into a reconstituted, second tissue sample image comprised of multiple image fields representing the second tissue;
  analyzing tissue regions of the second reconstituted tissue sample image using a second set of morphometric and texture features highly discriminating for the second precancerous tissue;
  combining the morphometric and texture feature measurements of the tissue regions from the first precancerous tissue to a common scale; and
  combining the morphometric and texture feature measurements of the tissue regions from the second precancerous tissue to the same common scale so that progression of cancer of the first and second tissues can be compared on the same basis.

33. A method in accordance with claim 32 wherein there is provided as first precancerous tissue a cervical tissue sample and wherein there is provided as the second precancerous tissue an esophageal tissue.

34. A method in accordance with claim 32 including the step of taking sequentially in time the first and second precancerous tissue samples from the same part of the body and using thereon the first and second sets of morphometric and texture features for analysis.

35. A method in accordance with claim 32 wherein the first and second precancerous tissues are taken from first and second parts of a body.

36. A method in accordance with claim 32 wherein the first and second precancerous tissues are taken from different animals.

37. A method in accordance with claim 32 including the steps of analyzing the first and second precancerous tissue over a plurality of tissue fields.

38. A method in accordance with claim 32 including the step of normalizing the measurements recording the scores on a scale that has plus and minus numbers below twenty (20).

39. A method in accordance with claim 32 including the step of measuring at least some of the first morphometric or texture features with scales or units different from the scales or units used to measure the second morphometric or texture features.

40. Apparatus for analyzing a tissue sample having a layer of adjacent, connected tissue cells for pre-invasive neoplasia, comprising:
  a scanning device for optically and microscopically scanning the tissue sample to provide magnified multiple image fields of the tissue sample;
  a recorder for electronically recording the magnified, multiple image fields;
  apparatus for forming a reconstituted, low magnification image comprised of the multiple image fields of the suspected neoplasia tissue;
  a display for displaying to a viewer a reconstituted, low magnification tissue image comprised of multiple image fields;

a selector allowing the viewer to select a region from the reconstituted, low magnification image for analyses at a higher resolution; and an analyzer for analyzing the selected tissue sample image fields of the selected region using at least one morphometric and texture measurement for adjacent, connected tissue cells predetermined to be indicative of the progression of pre-invasive neoplasia development in the tissue sample.

41. Apparatus in accordance with claim 40 wherein the analyzer for analyzing the texture of the selected tissue sample image fields comprises a means for measuring texture which includes an analysis of neighboring cells for optical densities above a predetermined threshold.

42. Apparatus in accordance with claim 41 wherein the cells are part of a tissue sample having a basal layer extending in a given direction; and the means for measuring the run length is configurable to analyzing neighboring cells in the given direction of the basal layer.

43. Apparatus in accordance with claim 40 wherein the analyzer for measuring texture comprises means for making at least one of a valley, slope or peak measurement.

44. Apparatus in accordance with claim 43 comprising means for measuring a coarseness of the texture by subtracting from the slope measurements, the peak and valley measurements.

45. Apparatus in accordance with claim 40 wherein the analyzer for measuring texture comprises means for making a Markovian Texture measurement.

46. Apparatus in accordance with claim 45 wherein the analyzed cells are human cervix tissue cells images and the means for measuring morphological texture includes means for the making of Markovian Texture measurements.

* * * * *